(12) United States Patent
Twidwell et al.

(10) Patent No.: US 12,290,552 B2
(45) Date of Patent: *May 6, 2025

(54) TOPICAL THERAPEUTIC FORMULATIONS

(71) Applicant: Hybrid Medical, LLC, Eden Prairie, MN (US)

(72) Inventors: Jeffry Twidwell, Wayzata, MN (US);
Joel Buckley, Plymouth, MN (US);
Harold Hoium, Eden Prairie, MN (US)

(73) Assignee: Hybrid Medical, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/126,901

(22) Filed: Mar. 27, 2023

(65) Prior Publication Data

US 2024/0050535 A1    Feb. 15, 2024

Related U.S. Application Data

(63) Continuation of application No. 14/977,300, filed on Dec. 21, 2015, now Pat. No. 11,622,997, which is a continuation of application No. 13/747,151, filed on Jan. 22, 2013, now Pat. No. 9,333,242.

(60) Provisional application No. 61/588,441, filed on Jan. 19, 2012.

(51) Int. Cl.
| | | |
|---|---|---|
| *A61K 38/44* | (2006.01) | |
| *A61K 9/00* | (2006.01) | |
| *A61K 9/06* | (2006.01) | |
| *A61K 9/12* | (2006.01) | |
| *A61K 31/277* | (2006.01) | |
| *A61K 31/40* | (2006.01) | |
| *A61K 31/4418* | (2006.01) | |
| *A61K 31/4422* | (2006.01) | |
| *A61K 31/554* | (2006.01) | |
| *A61K 45/06* | (2006.01) | |
| *A61K 47/24* | (2006.01) | |
| *A61P 17/00* | (2006.01) | |
| *A61P 19/04* | (2006.01) | |
| *C07D 211/90* | (2006.01) | |

(52) U.S. Cl.
CPC .......... *A61K 38/446* (2013.01); *A61K 9/0014* (2013.01); *A61K 9/06* (2013.01); *A61K 9/12* (2013.01); *A61K 31/277* (2013.01); *A61K 31/40* (2013.01); *A61K 31/4418* (2013.01); *A61K 31/4422* (2013.01); *A61K 31/554* (2013.01); *A61K 45/06* (2013.01); *A61K 47/24* (2013.01); *A61P 17/00* (2018.01); *A61P 19/04* (2018.01); *C07D 211/90* (2013.01); *C12Y 115/01001* (2013.01)

(58) Field of Classification Search
CPC .. A61K 2300/00; A61K 31/277; A61K 31/40; A61K 31/4422; A61K 31/554; A61K 38/446; A61K 31/4418; A61K 45/06; A61K 47/24; A61K 9/0014; A61K 9/06; A61K 9/12; C07D 211/90; C12Y 115/01001

See application file for complete search history.

(56) References Cited

U.S. PATENT DOCUMENTS

| | | | |
|---|---|---|---|
| 4,879,119 A * | 11/1989 | Konno | ................. A61K 9/7084 |
| | | | 424/448 |
| 5,006,333 A | 4/1991 | Saifer et al. | |
| 5,132,119 A | 7/1992 | Lee | |
| 5,229,130 A | 7/1993 | Sharma et al. | |
| 5,431,924 A | 7/1995 | Ghosh et al. | |
| 5,580,556 A | 12/1996 | Horrobin | |
| 5,629,019 A | 5/1997 | Lee et al. | |
| 5,747,043 A | 5/1998 | Ginoux et al. | |
| 5,958,384 A | 9/1999 | Holick | |
| 6,031,005 A | 2/2000 | Easterling | |
| 6,103,246 A | 8/2000 | Tisdale et al. | |
| 6,312,720 B1 | 11/2001 | Katinger et al. | |
| 6,328,987 B1 | 12/2001 | Marini | |
| 6,353,028 B2 * | 3/2002 | Easterling | ............... A61P 15/00 |
| | | | 424/78.02 |
| 6,375,986 B1 | 4/2002 | Ryde et al. | |
| 6,525,100 B1 | 2/2003 | Easterling | |

(Continued)

FOREIGN PATENT DOCUMENTS

| | | |
|---|---|---|
| CN | 101947312 A | 1/2011 |
| EP | 0131228 A2 | 1/1985 |

(Continued)

OTHER PUBLICATIONS

US 9,259,457 B2, 02/2016, Twidwell et al. (withdrawn)
"U.S. Appl. No. 13/747,151, Advisory Action mailed Nov. 19, 2014", 3 pgs.
"U.S. Appl. No. 13/747,151, Declaration Under 37 CFR 1.132 of Dr. Laurence A. Levine, dated Jun. 29, 2015", 3 pgs.
"U.S. Appl. No. 13/747,151, Examiner Interview Summary mailed Apr. 3, 2014", 3 pgs.
"U.S. Appl. No. 13/747,151, Examiner Interview Summary mailed Dec. 3, 2014", 4 pgs.

(Continued)

*Primary Examiner* — Michael B. Pallay
(74) *Attorney, Agent, or Firm* — Schwegman Lundberg & Woessner, P.A.

(57) ABSTRACT

The invention provides topical compositions and methods for using the compositions. The compositions can be used for the treatment of fibrotic or connective tissue disorders involving scarring, sub-dermal plaque accumulations, or fibrosis of muscle tissue. The disorders can be painlessly treated by the topical application of a composition described herein. One or more calcium channel blocker agents can serve as an active ingredient of the compositions, optionally in combination with, for example, one or more of emu oil and superoxide dismutase. The composition can further include pharmaceutically acceptable carriers that can facilitate the non-invasive transdermal delivery of the active(s) to subdermal sites.

19 Claims, No Drawings

(56) References Cited

U.S. PATENT DOCUMENTS

| | | | |
|---|---|---|---|
| 6,531,126 B2 | 3/2003 | Farmer | |
| 6,592,903 B2 | 7/2003 | Ryde et al. | |
| 6,627,663 B2 | 9/2003 | Easterling | |
| 6,733,751 B2 | 5/2004 | Farmer | |
| 6,969,529 B2 | 11/2005 | Bosch et al. | |
| 7,371,407 B2 | 5/2008 | Farmer | |
| 7,476,379 B1 | 1/2009 | Pearson et al. | |
| 7,851,431 B2 | 12/2010 | Easterling et al. | |
| 8,293,277 B2 | 10/2012 | Swanson et al. | |
| 9,238,059 B2* | 1/2016 | Twidwell | C12Y 115/01001 |
| 9,333,242 B2* | 5/2016 | Twidwell | A61K 31/4422 |
| 10,471,131 B2* | 11/2019 | Twidwell | C12Y 115/01001 |
| 11,446,363 B2* | 9/2022 | Twidwell | A61K 35/57 |
| 11,622,997 B2* | 4/2023 | Twidwell | A61K 31/554 |
| | | | 424/94.4 |
| 12,053,508 B2* | 8/2024 | Twidwell | A61K 31/554 |
| 2001/0033838 A1* | 10/2001 | Farmer | A61P 31/00 |
| | | | 424/522 |
| 2001/0047037 A1 | 11/2001 | Easterling | |
| 2002/0022664 A1 | 2/2002 | Easterling | |
| 2002/0151537 A1 | 10/2002 | Easterling | |
| 2004/0170675 A1 | 9/2004 | Easterling | |
| 2004/0171684 A1 | 9/2004 | Easterling | |
| 2008/0161782 A1 | 7/2008 | Chan et al. | |
| 2008/0274153 A1 | 11/2008 | Farmer | |
| 2009/0047209 A1 | 2/2009 | Merisko-Liversidge | |
| 2009/0087503 A1* | 4/2009 | Henderson | A61K 31/00 |
| | | | 514/1.1 |
| 2010/0055138 A1 | 3/2010 | Margulies et al. | |
| 2010/0221327 A1 | 9/2010 | Jenkins et al. | |
| 2013/0209545 A1 | 8/2013 | Twidwell et al. | |
| 2015/0150949 A1 | 6/2015 | Twidwell et al. | |
| 2015/0320816 A1 | 11/2015 | Patel | |
| 2016/0106816 A1 | 4/2016 | Twidwell et al. | |
| 2016/0129091 A1 | 5/2016 | Twidwell et al. | |
| 2020/0121764 A1 | 4/2020 | Twidwell et al. | |
| 2023/0082254 A1 | 3/2023 | Twidwell et al. | |

FOREIGN PATENT DOCUMENTS

| | | |
|---|---|---|
| EP | 2804606 B1 | 6/2017 |
| EP | 3269372 B1 | 6/2019 |
| JP | 61210024 A | 9/1986 |
| WO | WO-2013110077 A1 | 7/2013 |
| WO | WO-2015006469 A2 | 1/2015 |
| WO | WO-2017117268 A1 | 7/2017 |

OTHER PUBLICATIONS

"U.S. Appl. No. 13/747,151, Final Office Action mailed Aug. 14, 2014", 7 pgs.

"U.S. Appl. No. 13/747,151, Non Final Office Action mailed Apr. 6, 2015", 16 pgs.

"U.S. Appl. No. 13/747,151, Non Final Office Action mailed Nov. 21, 2013", 14 pgs.

"U.S. Appl. No. 13/747,151, Notice of Allowability mailed Apr. 12, 2016", 4 pgs.

"U.S. Appl. No. 13/747,151, Notice of Allowance mailed Apr. 12, 2016", 4 pgs.

"U.S. Appl. No. 13/747,151, Notice of Allowance mailed Sep. 15, 2015", 12 pgs.

"U.S. Appl. No. 13/747,151, Response filed Apr. 21, 2014 to Non Final Office Action mailed Nov. 21, 2013", 11 pgs.

"U.S. Appl. No. 13/747,151, Response filed Jul. 2, 2015 to Non Final Office Action mailed Apr. 6, 2015", 10 pgs.

"U.S. Appl. No. 13/747,151, Response filed Sep. 20, 2013 to Restriction Requirement mailed Jun. 20, 2013", 6 pgs.

"U.S. Appl. No. 13/747,151, Response filed Sep. 26, 2014 to Final Office Action mailed Aug. 14, 2014", 6 pgs.

"U.S. Appl. No. 13/747,151, Response filed Dec. 15, 2014 to Advisory Action mailed Nov. 19, 2014", 8 pgs.

"U.S. Appl. No. 13/747,151, Restriction Requirement mailed Jun. 20, 2013", 7 pgs.

"U.S. Appl. No. 13/747,151, Supplemental Amendment filed Aug. 3, 2015", 7 pgs.

"U.S. Appl. No. 14/610,875, Examiner Interview Summary mailed Jun. 25, 2015", 3 pgs.

"U.S. Appl. No. 14/610,875, Non Final Office Action mailed Apr. 3, 2015", 33 pgs.

"U.S. Appl. No. 14/610,875, Notice of Allowance mailed Sep. 10, 2015", 12 pgs.

"U.S. Appl. No. 14/610,875, Preliminary Amendment Filed Jan. 30, 2015", 7 pgs.

"U.S. Appl. No. 14/610,875, Response filed Jul. 2, 2015 to Non Final Office Action mailed Apr. 3, 2015", 13 pgs.

"U.S. Appl. No. 14/610,875, Supplemental Amendment filed Aug. 3, 2015", 6 pgs.

"U.S. Appl. No. 14/977,300 Response filed Aug. 11, 2017 to Final Office Action mailed Apr. 13, 2017", 9 pgs.

"U.S. Appl. No. 14/977,300, Advisory Action mailed Sep. 14, 2017", 3 pgs.

"U.S. Appl. No. 14/977,300, Examiner Interview Summary mailed Jan. 14, 2021", 3 pgs.

"U.S. Appl. No. 14/977,300, Examiner Interview Summary mailed Apr. 10, 2019", 3 pgs.

"U.S. Appl. No. 14/977,300, Examiner Interview Summary mailed Jul. 8, 2022", 2 pgs.

"U.S. Appl. No. 14/977,300, Final Office Action mailed Jan. 7, 2019", 19 pgs.

"U.S. Appl. No. 14/977,300, Final Office Action mailed Apr. 13, 2017", 14 pgs.

"U.S. Appl. No. 14/977,300, Final Office Action mailed Jun. 30, 2021", 20 pgs.

"U.S. Appl. No. 14/977,300, Non Final Office Action mailed Jun. 27, 2018", 19 pgs.

"U.S. Appl. No. 14/977,300, Non Final Office Action mailed Jul. 20, 2022", 10 pgs.

"U.S. Appl. No. 14/977,300, Non Final Office Action mailed Jul. 26, 2016", 9 pgs.

"U.S. Appl. No. 14/977,300, Non Final Office Action mailed Aug. 22, 2019", 18 pgs.

"U.S. Appl. No. 14/977,300, Non Final Office Action mailed Sep. 25, 2020", 18 pgs.

"U.S. Appl. No. 14/977,300, Notice of Allowance mailed Nov. 30, 2022", 9 pgs.

"U.S. Appl. No. 14/977,300, Preliminary Amendment filed Dec. 21, 2015", 3 pgs.

"U.S. Appl. No. 14/977,300, Response filed Jan. 26, 2017 to Non Final Office Action mailed Jul. 26, 2016", 9 pgs.

"U.S. Appl. No. 14/977,300, Response filed Mar. 24, 2021 to Non Final Office Action mailed Sep. 25, 2020", 9 pgs.

"U.S. Appl. No. 14/977,300, Response filed Oct. 19, 2022 to Non Final Office Action mailed Jul. 20, 2022", 6 pgs.

"U.S. Appl. No. 14/977,300, Response filed Oct. 29, 2018 to Non Final Office Action mailed Jun. 27, 2018", 12 pgs.

"U.S. Appl. No. 14/977,300, Response filed Jun. 25, 2019 to Final Office Action mailed Jan. 7, 2019", 9 pgs.

"U.S. Appl. No. 14/977,300, Response to Non Final Office Action mailed Aug. 22, 2019 filed Jul. 21, 2020", 10 pgs.

"U.S. Appl. No. 14/981,167, Advisory Action mailed Apr. 11, 2019", 3 pgs.

"U.S. Appl. No. 14/981,167, Advisory Action mailed Nov. 24, 2017", 4 pgs.

"U.S. Appl. No. 14/981,167, Examiner Interview Summary mailed Oct. 9, 2018", 3 pgs.

"U.S. Appl. No. 14/981,167, Final Office Action mailed Jan. 14, 2019", 7 pgs.

"U.S. Appl. No. 14/981,167, Final Office Action mailed Jun. 14, 2017", 31 pgs.

"U.S. Appl. No. 14/981,167, Non Final Office Action mailed Jul. 2, 2018", 21 pgs.

"U.S. Appl. No. 14/981,167, Non Final Office Action mailed Oct. 20, 2016", 36 pgs.

(56) References Cited

OTHER PUBLICATIONS

"U.S. Appl. No. 14/981,167, Notice of Allowance mailed Apr. 30, 2019", 7 pgs.
"U.S. Appl. No. 14/981,167, Notice of Allowance mailed Jun. 7, 2019", 7 pgs.
"U.S. Appl. No. 14/981,167, Notice of Allowance mailed Sep. 25, 2019", 8 pgs.
"U.S. Appl. No. 14/981,167, Response filed Feb. 20, 2017 to Non Final Office Action mailed Oct. 20, 2016", 8 pgs.
"U.S. Appl. No. 14/981,167, Response filed Apr. 4, 2019 to Final Office Action mailed Jan. 14, 2019", 6 pgs.
"U.S. Appl. No. 14/981,167, Response filed Aug. 23, 2016 to Restriction Requirement mailed May 23, 2016", 6 pgs.
"U.S. Appl. No. 14/981,167, Response filed Oct. 22, 2018 to Non Final Office Action mailed Jul. 2, 2018", 12 pgs.
"U.S. Appl. No. 14/981,167, Response filed Dec. 14, 2017 to Final Office Action mailed Jun. 14, 2017", 15 pgs.
"U.S. Appl. No. 14/981,167, Restriction Requirement mailed May 23, 2016", 7 pgs.
"U.S. Appl. No. 14/981,167, Response filed Apr. 18, 2019 to Final Office Action mailed Jan. 14, 2019", 6 pgs.
"U.S. Appl. No. 16/666,027, Advisory Action mailed Feb. 22, 2022", 3 pgs.
"U.S. Appl. No. 16/666,027, Final Office Action mailed Nov. 17, 2021", 16 pgs.
"U.S. Appl. No. 16/666,027, Non Final Office Action mailed Sep. 28, 2020", 8 pgs.
"U.S. Appl. No. 16/666,027, Notice of Allowability mailed Aug. 29, 2022", 3 pgs.
"U.S. Appl. No. 16/666,027, Notice of Allowance mailed May 12, 2022", 9 pgs.
"U.S. Appl. No. 16/666,027, Response filed Feb. 14, 2022 to Final Office Action mailed Nov. 17, 2021", 12 pgs.
"U.S. Appl. No. 16/666,027, Response filed Mar. 25, 2021 to Non Final Office Action mailed Sep. 28, 2020", 7 pgs.
"U.S. Appl. No. 16/666,027, Response filed Aug. 6, 2021 to Restriction Requirement mailed Jun. 17, 2021", 5 pgs.
"U.S. Appl. No. 16/666,027, Restriction Requirement mailed Jun. 17, 2021", 5 pgs.
"U.S. Appl. No. 17/891,835, Non Final Office Action mailed May 25, 2023", 7 pgs.
"U.S. Appl. No. 17/891,835, Preliminary Amendment filed Dec. 1, 2022", 5 pgs.
"U.S. Appl. No. 17/891,835, Response filed Mar. 21, 2023 to Restriction Requirement mailed Jan. 20, 2023", 6 pgs.
"U.S. Appl. No. 17/891,835, Restriction Requirement mailed Jan. 20, 2023", 5 pgs.
"Declaration Under 37 C.F.R. 1.132 signed by Daniel Moudry on Apr. 19, 2014", 3 pgs.
"Declaration Under 37 C.F.R. 1.132 signed by Harold Holum on Apr. 20, 2014", 8 pgs.
"Declaration Under 37 C.F.R. 1.132 signed by Jeff Twidwell on Dec. 14, 2014", 3 pgs.
"Declaration Under 37 C.F.R. 1.132 signed by Laurence A. Levine on Jun. 29, 2015", 3 pgs.
"Declaration Under 37 C.F.R. 1.132 signed by Marc Blasser on Jun. 30, 2015", 3 pgs.
"European Application Serial No. 13738804.7, Communication pursuant to Article 94(3) EPC mailed Aug. 3, 2016", 3 pgs.
"European Application Serial No. 13738804.7, Examination Notification Art. 94(3) mailed Jan. 14, 2016", 3 pgs.
"European Application Serial No. 13738804.7, Extended European Search Report mailed Mar. 11, 2015", 7 pgs.
"European Application Serial No. 13738804.7, Office Action mailed Mar. 27, 2015", 1 pg.
"European Application Serial No. 13738804.7, Office Action mailed Sep. 4, 2014", 3 pgs.
"European Application Serial No. 13738804.7, Response filed Feb. 9, 2015 to Office Action mailed Sep. 4, 2014", 6 pgs.
"European Application Serial No. 13738804.7, Response filed May 24, 2016 to Examination Notification Art. 94(3) mailed Jan. 14, 2016", 9 pgs.
"European Application Serial No. 13738804.7, Response filed Sep. 29, 2016 to Communication pursuant to Article 94(3) EPC mailed Aug. 3, 2016", 15 pgs.
"European Application Serial No. 13738804.7, Response filed Oct. 5, 2015 to Office Action mailed Mar. 27, 2015", 14 pgs.
"European Application Serial No. 17176955.7, Communication Pursuant to Article 94(3) EPC mailed Oct. 25, 2018", 3 pgs.
"European Application Serial No. 17176955.7, Extended European Search Report mailed Dec. 15, 2017", 9 pgs.
"European Application Serial No. 17176955.7, Response filed Jul. 12, 2018 to Extended European Search Report mailed Dec. 15, 2017", 10 pgs.
"European Application Serial No. 17176955.7, Response filed Dec. 20, 2018 to Communication Pursuant to Article 94(3) EPC mailed Oct. 25, 2018", 114 pgs.
"International Application Serial No. PCT/US2013/022568, International Preliminary Report on Patentability mailed Jul. 31, 2014", 6 pgs.
"International Application Serial No. PCT/US2013/022568, International Search Report mailed Apr. 25, 2013", 3 pgs.
"International Application Serial No. PCT/US2013/022568, Written Opinion mailed Apr. 25, 2013", 4 pgs.
"International Application Serial No. PCT/US2016/068966, International Preliminary Report on Patentability mailed Jul. 12, 2018", 9 pgs.
"International Application Serial No. PCT/US2016/068966, International Search Report mailed Apr. 19, 2017", 6 pgs.
"International Application Serial No. PCT/US2016/068966, Written Opinion mailed Apr. 19, 2017", 7 pgs.
Cataldi, M., et al., "1,4-Dihydropyridines: The Multiple Personalities of a Blockbuster Drug Family", Translational Medicine, 4, (2012), 12-26.
Cataldi, Mauro, et al., "1,4-Dihydropyridines: The Multiple Personalities of a Blockbuster Drug Family", Translational Medicine, 4(2), (2012), 15 pgs.
Cavallini, Giorgio, et al., "Open Preliminary Randomized Prospective Clinical Trial of Efficacy and Safety of Three Different Verapamil Dilutions for Intraplaque Therapy of Peyronie's Disease", Urology 69, (2007), 950-954.
Chiumiento, A., et al., "Anti-inflammatory properties of superoxide dismutase modified with carboxymetil-cellulose polymer and hydrogel", J Mater Sci: Mater Med, 17, (2006), 427-435.
Chiumiento, A., et al., "Immobilizing Cu, Zn-Superoxide Dismutase in Hydrogels of Carboxymethylcellulose Improves Its Stability and Wound Healing Properties", Biochemistry (Moscow), 71(12), (2006), 1324-1328.
Derrer, "Connective Tissue Disorder, types, symptoms and causes", Webmed, (2013), 1-4.
Edraki, et al., "Dihydropyridines: evaluation of their current and future pharmacological applications", Drug Discovery Today, vol. 14, (Nov. 2009), 1058-1066.
Ehdaie, Behzad, "Enhanced Delivery of Transdermal Drugs Through Human Skin With Novel Carriers", J. Pharm. Biomed. Sci., 1 (8), (2011), 161-166.
Eisenberg, Mark J, et al., "Calcium Channel Blockers: An Update", The American Journal of Medicine, vol. 116, (Jan. 1, 2004), 35-43.
Elliott, William J, et al., "Calcium Channel Blockers", The Journal of Clinical Hypertension, 13(9), (Sep. 2011), 687-689.
Epstein, Murray, "The Calcium Antagonist Controversy: The Emerging Importance of Drug Formulation as a Determinant of Risk", The American Journal of Cardiology, 79(10A), (May 22, 1997), 9-19.
Fitch, William P., et al., "Topical Verapamil HCl, Topical Trifluoperazine, and Topical Magnesium Sulfate for the Treatment of Peyronie's Disease—A Placebo-Controlled Pilot Study", J Sex Med, 4, (2007), 477-484.
Freedman, D.D., et al., "'Second generation' dihydropyridine calcium antagonists. Greater vascular selectivity and some unique applications", Drugs, 34 (abstract only), (Nov. 1987), 1 pg.
Freedman, Donna D, et al., "'Second generation' dihydropyridine calcium antagonists. Greater vascular selectivity and some unique

(56) References Cited

OTHER PUBLICATIONS applications (Abstract Only)", Drugs, 34(5), [Online] Retrieved from the internet on Jun. 26, 2019: <URL: https://www.ncbi.nlm.nih.gov/pubmed/3319491>, (1987), 2 pgs.

Frishman, William H, "Calcium Channel Blockers: Differences Between Subclasses", American Journal of Cardiovascular Drugs, 7(1), (2007), 17-23.

Garay-Arroyo, Adriana, et al., "Cu, Zn-superoxide dismutase of *Saccharomyces cerevisiae* is required for resistance to hyperosmosis", FEBS Letters, 539, (2003), 68-72.

Godfraind, Theophile, et al., "Calcium Antagonism and Calcium Entry Blockade", Pharmacological Reviews, 38(4), (1986), 321-416.

Godfraind, Theophile, "Discovery and Development of Calcium Channel Blockers", Frontiers in pharmacology, vol. 8, Art. 286, (May 29, 2017), 25 pgs.

Greenfield, Jason M., et al., "Verapamil Versus Saline in Electromotive Drug Administration for Peyronie's Disease: A Double-Blind, Placebo Controlled Trial", The Journal of Urology, 177, (Mar. 2007), 972-975.

Hauck, E. W, et al., "A Critical Analysis of Nonsurgical Treatment of Peyronie's Disease", European Urology 49, (2006), 987-997.

Hemmati, A.A., et al., "Wound Healing Potential of Topical Amlodipine in Full Thickness Wound of Rabbit", Jundishapur J. Nat. Pharm. Prod., 9, (Aug. 2014), 4 pgs.

Inal, T, et al., "Effect of intralesional interferon-alpha 2b combined with oral vitamin E for treatment of early stage Peyronie's disease: a randomized and prospective study", Urology, 67(5), (May 2006), 1038-1042.

Ivanov, V., et al., "Inhibition of collagen synthesis by select calcium and sodium channel blockers can be mitigated by ascorbic acid and ascorbyl palmitate", Am. J. Cardiovasc. Dis., 6, (2016), 26-35.

Ivanov, Vadim, et al., "Inhibition of collagen synthesis by select calcium and sodium channel blockers can be mitigated by ascorbic acid and ascorbyl palmitate", Am J Cardiovasc Dis., 6(2), (2016), 26 pgs.

Kuehhas, et al., "Peyronie's disease: nonsurgical therapy options", Reviews in Urology, 2011, vol. 13, (2011), 139-146.

Lalani, J., et al., "Protein-Functionalized PLGA Nanoparticles of Lamotrigine for Neuropathic Pain Management", AAPS PharmSciTech, 16, (Apr. 2015), 413-427.

Levine, Laurence, "Comment on Topical Verapamil HCL, Topical Trifluoroperazine, and Topical Magnesium Sulfate for the Treatment of Peyronie's Diseease—A Placebo-Controlled Pilot Study", J Sex Med, 4, (2007), 1081-1082.

Lohcharoenkal, W., et al., "Protein Nanoparticles as Drug Delivery Carriers for Cancer Therapy", BioMed Research International, vol. 2014, Article ID 180549, Hindawi Publishing Corporation, (2014), 12 p.

Martin, David J., et al., "Transdermal Application of Verapamil Gel to the Penile Shaft Fails to Infiltrate the Tunica Albuginea", The Journal of Urology, 168, 2483-2485.

Meredith, et al., "Dihydropyridine calcium channel blockers: basic pharmacological similarities but fundamental therapeutic differences", Journal of Hypertension, vol. 22, (2004), 1641-1648.

Neychev, H, et al., "Antiinflammatory effect of superoxide dismutase(SOD). Comparison between yeast and bovine SOD on some complement-mediated reactions in vitro and in vivo", Int. J. Tissue React. 1994, vol. 16, (1994), 131-137.

Okoro, Uchechi, et al., "Chapter 6. Nanoparticles for Dermal and Transdermal Drug Delivery", In: Application of Nanotechnology in Drug Delivery, (2014), 193-235.

Qi, J, et al., "A Novel Conjugate of Low-Molecular-Weight Heparin and Cu, Zn-Superoxide Dismutase: Study on Its Mechanism in preventing Brain Reperfusion Injury after Ischemia in Gerbils", Brain Res, (Jan. 17, 2009), 1 pg.

Riedl, Claus R., et al., "Liposomal Recombinant Human Superoxide Dismutase for the Treatment of Peyronie's Disease: A Randomized Placebo-Controlled Double-Blind Prospective Clinical Study", Eurpoean Urology, 48, 656-661.

Riedl, Claus R., et al., "Pilot Study on Liposomal Recombinant Human Superoxide Dismutase for the Treatment of Peyronie's Disease", Eur Urol 2001: 40, (2001), 343-349.

Roth, M., et al., "Ca2+ channel blockers modulate metabolism of collagens within the extracellular matrix", Proc. Natl. Acad. Sci. USA, 93, (May 1996), 5478-5482.

Roth, Michael, et al., "Ca(2)(Plus) channel blockers modulate metabolism of collagens within the extracellular matrix", Proc. Natl. Acad. Sci. USA, vol. 93, 5 pgs.

Sekine, Takashi, et al., "Gel Ointment of Verapamil for Percutaneous Absorption", Drug Design and Delivery, 1, (1987), 245-252.

Soh, J., et al., "Nicardipine vs. Saline Injection as Treatment for Peyronie's Disease: A Prospective, Randomized, Single-Blind Trial", J Sex Med, 7, (2010), 3743-3749.

Toal, C.B., et al., "Long-acting dihydropyridine calcium-channel blockers and sympathetic nervous system activity in hypertension: A literature review comparing amlodipine and nifedipine GITS", Blood Pressure, 21:sup1, (2012), 3-10.

Toal, Corey B, et al., "Long-acting dihydropyridine calcium-channel blockers and sympathetic nervous system activity in hypertension: A literature review comparing amlodipine and nifedipine GITS", Blood Pressure, 21 (Suppl 1), (Jul. 5, 2012), 9 pgs.

Triggle, David J, "Calcium channel antagonists: Clinical uses—Past, present and future", Biochemical Pharmacology, 74(1), (2007), 9 pgs.

Trivino, A., et al., "Drug-Excipient Compatibility for the Formulation Development of Solid Lipid Nanoparticles", American Pharmaceutical Review, Retrieved from the Internet: <URL: http://www.americanpharmaceuticalreview.com/Featured-Articles/173074-Drug-Excipient-Compatibility-for-the-Formulation-Development-of-Solid-Lipid-Nanoparticles/>, (Apr. 2, 2015), 6 pgs.

Trost, Landon W., et al., "Pharmacological Management of Peyronie's Disease", Drugs, 67 (4), (2007), 527-545.

Twidwell, J., et al., "Topical treatment for acute phase Peyronie's disease utilizing a new gel, H-100: a randomized, prospective, placebo-controlled pilot study", Int. J. Impot. Res., 28, (Dec. 24, 2015), 41-45.

Umut, E., "Surface Modification of Nanoparticles Used in Biomedical Applications", Modern Surface Engineering Treatments, Chapter 8, Mahmood Aliofkhazrael (ed.) Retrieved from the Internet: <URL: http://www.intechopen.com/books/modern-surface-engineering-treatments/surface-modification-of-nanoparticles-used-in-biomedical-applications>, (May 22, 2013), 185-208.

Van Zwieten, P.A., et al., "Similarities and differences between calcium antagonists: pharmacological aspects", J. Hypertens. Suppl., 11 (abstract only), (Mar. 1993), 1 pg.

Van Zwieten, P.A., et al., "Similarities and differences between calcium antagonists: pharmacological aspects", J Hypertens Suppl., 11(1), (Mar. 1993), S3-11.

Weiner, Donald A, "Calcium Channel Blockers", Medical Clinics of North America, 72(1), (1988), 83-115.

Willimann, H., et al., "Lecithin organogel as Matrix for Transdermal Transport of Drugs", Journal of Pharmaceutical Sciences, 81 (9), (Nov. 1992), 871-874.

Winfield, "Connective tissue diseases", Lever's Histopathology of the Skin, 10th ed. Philadelphia: Lippincott Williams & Wilkins 2009, Chapter 10, Connective tissue diseases, (2009), 329-364.

Wray, "Dermal and subcutaneous Tumor Part I", PowerPoint presentation, (2005), 1-76.

Wray, "Dermal and subcutaneous Tumor Part II", PowerPoint presentation, (2005), 1-76.

Zhang, H. W., et al., "Characterization and Stability Investigation of Cu, Zn-Superoxide Dismutase Covalently Modified by Low Molecular Weight Heparin", Biochemistry (Moscow), (71) 1, (2006), S96-S100.

U.S. Appl. No. 17/891,835, Examiner Interview Summary mailed Jan. 24, 2024, 2 pgs.

U.S. Appl. No. 17/891,835, Final Office Action mailed Dec. 26, 2023, 6 pgs.

U.S. Appl. No. 17/891,835, Notice of Allowance mailed Mar. 27, 2024, 8 pgs.

U.S. Appl. No. 17/891,835, Response filed Feb. 26, 2024 to Final Office Action mailed Dec. 26, 2023, 6 pgs.

(56) References Cited

OTHER PUBLICATIONS

U.S. Appl. No. 17/891,835, Response filed Oct. 25, 2023 to Non Final Office Action mailed May 25, 2023, 6 pgs.

* cited by examiner

TOPICAL THERAPEUTIC FORMULATIONS

RELATED APPLICATIONS

This application is a continuation and claims the benefit of priority under 35 U.S.C. § 120 to U.S. patent application Ser. No. 14/977,300, filed on Dec. 21, 2015, which is a continuation and claims the benefit of priority under 35 U.S.C. § 120 to U.S. patent application Ser. No. 13/747,151, filed on Jan. 22, 2013, now U.S. Pat. No. 9,333,242, issued on May 10, 2016, which claims the benefit of priority under 35 U.S.C. § 119 (e) to U.S. Provisional Patent Application No. 61/588,441, filed on Jan. 19, 2012, which are hereby incorporated herein by reference in their entireties.

BACKGROUND OF THE INVENTION

Peyronie's disease has been known as a distinct malady for hundreds of years. The plaque of Peyronie's disease may develop following trauma to the penis that causes localized internal bleeding. While the symptoms and severity of the disease can vary, a common manifestation is a lump, plaque or scar tissue in the non-erect penis. The condition can result in painful erections and penile disfigurement, and is often associated with impotence.

Approximately one to ten percent of the male population experiences an incidence of Peyronie's disease in their lifetime. About 30 percent of men with Peyronie's disease also develop fibrosis (hardened cells) in other elastic tissues of the body, often in the hand or foot. Dupuytren's contracture of the hand and Ledderhose Fibrosis of the foot are examples of these conditions.

Peyronie's disease is typically treated with largely experimental approaches. Treatments that lack efficacy are discontinued and seemingly helpful treatments are continued. Surgery is the only current treatment for Peyronie's disease that has predictable efficacy. However, surgery can be undesirable and is usually indicated only after the disease has stabilized and the deformity prevents intercourse or causes extreme pain. Furthermore, surgery can result in various complications including a permanent shortening of the penis. While surgical intervention is currently the most effective treatment for a severe case of Peyronie's disease, the condition can reappear even after surgery.

There is a still a very strong need for effective therapies for Peyronie's disease and related connective tissue disorders. Most non-surgical treatments for Peyronie's disease are largely ineffective. Limited success has been found with intra-lesional injections of agents such as verapamil and clostridial collagenase. Laser technology has emerged as a means of reducing plaques and fibrosis. Unfortunately, the effectiveness of this approach has not been completely confirmed. The variety of treatment options for Peyronie's disease is testament to the serious need that remains for an effective treatment. A treatment is needed that would be tolerable to the patient in terms of cost, convenience, and comfort.

SUMMARY

Connective tissue disorders manifested by sub-dermal plaque accumulations can result in localized pain and partial or total erectile dysfunction. Fibrosis of neighboring muscle tissues can further complicate the condition. Examples of sub-dermal plaque accumulation disorders include Peyronie's Disease, Ledderhose Fibrosis, Dupuytren's contracture of the hand, and certain forms of erectile dysfunction. The present invention provides compositions and methods for topically treating Peyronie's Disease, Dupuytren's hand contracture, Ledderhose Fibrosis, scarring, and erectile dysfunction arising from plaque accumulation.

In one embodiment, the invention provides a composition suitable for topical application to the skin for the treatment of Peyronie's Disease, Dupuytren's hand contracture, Ledderhose Fibrosis, scarring, or erectile dysfunction arising from plaque accumulation. The composition can include a calcium channel blocker active agent, superoxide dismutase, or both, in combination with emu oil. The composition can further include a pharmaceutically acceptable carrier, and optional fragrances, moisturizers, penetration enhancers, or a combination thereof. In one embodiment, the calcium channel blocker is nicardipine or verapamil. In some embodiments, the composition includes superoxide dismutase. The composition can include one or more non-invasive transdermal carrier agents, one or more penetration enhancers, or a combination thereof. The composition can be in the form of a gel, cream, foam, lotion, oil, ointment, paste, suspension, or aerosol spray.

The invention also provides methods for treating a connective tissue disorder, wherein the connective tissue disorder comprises sub-dermal plaque accumulation or scar tissue. The method can include topically or transdermally administering an effective amount of a composition described herein to a portion of the dermis that overlies a sub-dermal plaque or scar tissue. The application can be carried out for a period of time sufficient to reduce the symptoms or severity of the connective tissue disorder. The connective tissue disorder can be, for example, Peyronie's disease, Dupuytren's hand contracture, or Ledderhose Fibrosis, which disorders can include the manifestation of sub-dermal plaque accumulations or scar tissue. The administration of the composition can be, for example, about once or twice daily for a period of at least three weeks, or any other period of time prescribed by an attending clinician.

Thus, the invention provides for the compositions described herein for use in medical therapy. The medical therapy can be treating a connective tissue disorder such as Peyronie's disease, Dupuytren's hand contracture, Ledderhose Fibrosis, or a related condition. The invention also provides for the use of a composition as described herein for the manufacture of a medicament to treat a disease or condition in a human. The medicament can include a pharmaceutically acceptable diluent, excipient, or carrier.

DETAILED DESCRIPTION

Peyronie's disease may develop following trauma to the penis that causes localized internal bleeding, and can result in painful erections and penile disfigurement. The physical structure of the penis includes the corpora cavernosa—two erectile rods, the urethra—a conduit through which urine flows from the bladder, and the tunica, which separates the cavernosa from the outer layers of skin of the penis. Peyronie's disease can involve the formation of a plaque or scar tissue between the tunica and the outer layers of the skin (e.g., subdermal scar tissue). Scaring or plaque accumulation of the tunica reduces its elasticity. The result is that the affected area does not have the same elasticity as the surrounding, unaffected tissues. As the penis with Peyronie's disease becomes erect, the erect penis often bends in the direction of the scar tissue, which can cause varying amounts of pain.

A mild case of Peyronie's disease can heal spontaneously in six months to a year and a half. In severe cases, however, the hardened plaque substantially reduces penile flexibility and can cause excruciating pain where the penis is forced into a highly arcuate or even serpentine configuration upon erection. Plaques can cause the penis to bend upward, downward, and in some cases, when plagues develops on both top and bottom, the plaques can lead to indentation and shortening of the penis. In all but the mildest cases of Peyronie's disease, the subject suffers some degree of sexual dysfunction. In severe cases, sexual intercourse can be so painful that it is effectively prohibitive.

The plaque of Peyronie's disease may develop following trauma to the penis that causes localized internal bleeding. If the penis is abnormally bumped or bent, an area where the septum attaches to the elastic fibers surrounding the corpora cavernosa may stretch beyond its normal limit, which can injure the lining of the erectile chamber by, for example, rupturing small blood vessels. A damaged area may heal slowly or abnormally because of a combination of factors including repeated trauma and a naturally low amount of blood-flow in the sheath-like fibers of the elastic structures of the penis. In mild cases of Peyronie's disease (those that tend to heal within about a year), the plaque does not tend to advance beyond an initial inflammatory phase. In more severe cases, the plaque can undergo the formation of a tough fibrous tissue, called a fibrosis. These tissues can further undergo the formation of calcium deposits called calcification. Effective treatments for the causes and symptoms of Peyronie's disease and other connective tissue disorders would provide welcome relief from the difficulties associated with these serious conditions. Such effective treatments are described herein below.

Definitions

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more ingredients can refer to one; one or two; one, two, or three; one two, three, or four; five, six, seven, eight, nine, or about ten ingredients.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo. A composition described herein is typically contacted to the skin above sub-dermal plaque accumulation or scar tissue of a subject seeking treatment.

An "effective amount" refers to an amount effective to treat a disease, disorder, and/or condition, or to bring about a recited effect. For example, an amount effective can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

"Penetration enhancement" or "permeation enhancement" refers to an increase in the permeability of the skin or mucosal tissue to a pharmacologically active agent in the presence of a penetration enhancer, i.e., so that the rate at which the agent permeates the skin (i.e., the "flux" of the agent through the body surface) is increased relative to the rate that would be obtained in the absence of penetration enhancer. The enhanced permeation effected through the use of such enhancers can be observed by measuring the rate of diffusion of an active through animal or human skin using, for example a Franz diffusion apparatus, as known in the art.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" extend to prophylaxis and include prevent, prevention, preventing, lowering, stopping or reversing the progression or severity of the condition or symptoms being treated. As such, the term "treatment" includes medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "subdermal plaque accumulation" refers to conditions such as Peyronie's disease, Dupuytren's contracture, Ledderhose Fibrosis, and/or scarring of tissue. The compositions described herein can treat, or reduce or alleviate the symptoms of, such conditions.

Emu Oil

Emu oil is an oil obtained from the fat of the emu, *Dromaius novaehollandiae*, a flightless bird, indigenous to Australia and New Zealand. Pure emu oil is typically a yellow liquid containing approximately 70% unsaturated fatty acid triglycerides by weight. The largest unsaturated fatty acid component of the triglycerides is oleic acid, a mono-unsaturated omega-9 fatty acid. Emu oil triglycerides can also include about 20% linoleic acid (an omega-6 fatty acid) and 1-2% linolenic acid (an omega-3 fatty acid). Fully refined emu oil certified by the American Emu Association has a moisture content below 0.10% by weight.

Emu oil typically has less than 3 wt. % of free fatty acids, and more commonly less than about 1.5 wt. % of free fatty acids, less than about 1.0 wt. % of free fatty acids, or less than about 0.5 wt. % of free fatty acids. Substantially all fatty acid moieties in emu oil are conjugated to glycerol in the form of triglycerides. Refined emu oil is essentially 100% triglycerides in composition, typically at least about 99.9% triglycerides. The specific mix of fatty acids can be specie specific, and the order of attachment of the three fatty acids to the glycerol molecule to form the triglyceride can also be specie specific. The composition of fatty acid moieties of emu oil is shown in Table 1.

TABLE 1

Emu Oil Average Triglyceride Fatty Acid Composition.

| FA Moiety | Average | Range (±3 SD) |
|---|---|---|
| C-14:0 (Myristic): | 0.4% | 0.17-0.68% |
| C-16:0 (Palmitic): | 21.5% | 17.5-26.5% |
| C-16:1 (Palmitoleic): | 3.7% | 1.2-5.7% |
| C-18:0 (Stearic): | 10.6% | 7.2-12% |
| C-18:1 (Oleic): | 51.4% | 38.4-56.4% |
| C-18:2 (Linoleic): | 12.7% | 6.2-24.2% |
| C-18:3 (Linolenic): | 0.9% | 0.1-2% |
| Calculated Iodine Value: | 69.7 | 69-71 |
| Free Fatty Acid: | 0.05% | <0.33% |
| Peroxide Value: | 1.53% | 1.5% |
| Moisture: | <0.03% | <0.03% |

Refined emu oil can be substantially 100% triglycerides having about 32% saturated fatty acid moieties, about 51% monounsaturated fatty acid moieties, and about 16% polyunsaturated fatty acid moieties. The polyunsaturated fatty acid moieties can be about 12-15% linoleic acid moieties and about 1% linolenic acid moieties, however the emu oil derived from some species of emu can include as much as 18% linoleic acid moieties. The compositions described herein preferably use fully refined Grade A emu oil certified by the American Emu Association. Emu oil is further described in U.S. Pat. No. 7,371,407 (Farmer). Examples of specific emu oil triglycerides as determined by HPLC analysis are shown in Table 2 below.

TABLE 2

Major Emu Oil Triglycerides.

| Sample | Triglycerides | Mean (%)/1 SD | Range (±3 SD) |
|---|---|---|---|
| A | LLL, OLLn, PLLn | 1.0/0.5 | 0.1-2.5 |
| B | OLL, PLL | 10.0/2.0 | 4.0-16.0 |
| C | OOL, POL, SLL | 28.2/4.2 | 15.6-40.8 |
| D | OOO, POO, PPO, SOL | 48.2/5.0 | 33.2-63.2 |
| E | POS | 5.8/0.8 | 3.4-8.2 | where P = palmitic, S = stearic, O = oleic, L = linoleic, and Ln = linolenic.

Pracaxi Oil

Pracaxi oil is the oil of the seeds of the *Pentaclethra macroloba* tree, commonly found throughout northern Brazil. The oil has high moisturizing activity and can improve skin tone and help retain elasticity. Pracaxi oil has a high behenic acid content and contains about 2 wt. % stearin. Pracaxi oil contains lauric acid (<0.12%), myristic acid (<0.43%), palmitic acid (<5%), palmitoleic acid (<5%), stearic acid (<5%), oleic acid (35-75%), arachidic acid (<1%), linoleic acid (10-25%), linolenic acid (<0.5%), gadoleic acid (<1.5%), behenic acid (10-25%), euricic acid (<1%), and lignoceric acid (10-15%) (approximate amounts). The pracaxi oil can be combined with other components to provide a carrier oil composition. Examples of suitable pracaxi oil compositions that can be used include a collagenase hyaluronidase topical gel, a dimethyl sulfone tranilast ascorbic acid topical gel, and a dimethyl sulfone ascorbic acid caffeine topical gel.

In some embodiments, the emu oil can be replaced with pracaxi oil or a pracaxi oil composition. Alternatively, a portion of the emu oil can be replaced with pracaxi oil or a pracaxi oil composition. For example, about 5%, 10%, 20%, 25%, 40%, 50%, 60%, 75%, 80%, 90%, or 95% of the emu oil in a composition can be replaced with pracaxi oil/composition.

Calcium Channel Blockers

A calcium channel blocker is a compound that disrupts the movement of calcium ($Ca^{2+}$) through calcium channels. A calcium channel blocker can also be referred to as a calcium channel blocker agent, a calcium channel blocker active agent, or a calcium ion channel blocker, and the like. Calcium channel blockers can block voltage-gated calcium channels (VGCCs) in blood vessels, which can decrease intracellular calcium leading to a reduction in muscle contraction. The topical compositions described herein will typically include a calcium channel blocker as an active agent.

One active ingredient in a topical formulation can be the calcium channel blocker nicardipine. Another active ingredient in a topical formulation can be the calcium channel blocker verapamil. Another active ingredient in a topical formulation can be the calcium channel blocker nifedipine. Other calcium channel blockers, topically applied with the novel compositions described herein, can provide similar therapeutic results. As would be readily recognized by one of skill in the art, the active can be included in the formulation as a salt. For example, reference to verapamil includes its salts, such as verapamil hydrochloride.

Combinations of calcium channel blocker active agents can have even greater efficacy than a single type of active. In some embodiments, an amount of a dihydropyridine calcium channel blocker, such as nicardipine, can be combined with various proportions of a diphenylalkylamine calcium channel blocker, such as verapamil. In other embodiments, various proportions of nicardipine can be combined with various proportions of a dihydropyridine calcium channel blocker such as nifedipine. Other calcium channel blockers that can be used in the compositions described herein, in any combination, include benzothiazepines such as diltiazem, other dihydropyridines such as amlodipine, felodipine, isradipine, nimodipine, and/or nisoldipine, and fast sodium inward channel inhibitors such as bepridil. An effective dose of a calcium channel blocker can be about 5 mg, about 10 mg, about 15 mg, about 20 mg, about 25 mg, about 30 mg, about 40 mg, about 50 mg, about 75 mg, or about 100 mg.

Superoxide Dismutase (SOD)

Superoxide dismutase (SOD) enzymes are a class of enzymes that catalyze the destruction of the superoxide free radical ($O^{2-}$), for example, the dismutation of superoxide into hydrogen peroxide and oxygen or hydrogen peroxide and water. They are an important antioxidant defense in nearly all cells exposed to oxygen. Superoxide dismutase consists of two subunits of identical molecular weight joined by a disulfide bond. The molecular weight of SOD is approximately 32.5 kDa. One suitable type of SOD is SOD derived from bacterial source, such as *Escherichia coli*, or a natural yeast strain of *Saccharomyces cerevisiae*, which is not conjugated or encapsulated. The SOD can be in the form of a powder, such as a lyophilized powder. Such forms of SOD are available from suppliers such as Professional Compounding Centers of America (Houston, TX) or Sigma-Aldrich (St. Louis, MO). The SOD used can be a commercial variety such as CAS #9054-89-1, SOD Activity 45000-55000 piu/mL, pH 7-9, very slight greenish liquid, heavy metal content<2 ppm (Pb, Cd, Co, Cr, Ni). The SOD can have an activity of ≥1,000 units/mg protein, ≥2,500 units/mg protein, about 1,000 to about 4,000 units/mg protein, or about 2,500 to about 6,000 units/mg protein. Another suitable type of SOD is the liposomally encapsulated recombinant human Cu/Zn-Superoxide Dismutase (lrhSOD) (approximately 1.4 mg total SOD per day; BID). The lrhSOD is available from suppliers such as Polymun Scientific, Vienna, Austria. Pharmaceutical grade Cu/Zn-Superoxide Dismutase is also known as orgotein. Other forms of SOD that can be used in formulations described herein include SOD conjugates such as polyethylene glycol-superoxide dismutase (PEG-SOD) and SOD conjugated to low molecular weight heparin (LMWH-SOD). In typical embodiments, suitable forms of SOD will not be derived from bovine sources.

Recombinant human Cu/Zn-SOD can be obtained and purified from *E. coli*, for example, as produced at the Institute of Applied Microbiology, in pharmaceutical grade quality (Vorauer-Uhl and Skias, *J. Chromatogr.* 1992; 625: 217-226). Liposomes of dipalmitoyl-phosphatidyl-choline (DPPC, Avanti Polar Lipids, Alabaster, AL, USA), cholesterol (Avanti Polar Lipids), and stearylamine (Sigma, St. Louis, MO, USA) with a molar ratio of 7/2/1 were produced by a modified ethanol injection method under sterile conditions (Naeff, *Adv. Drug Deliv. Rev.* 1996; 18: 343-347). Rh Cu/Zn-SOD liposomes were produced in phosphate-buffered saline.

The average diameter of the applied liposomes was about 200 nm with a polydispersity index of 0.2. Measurements were performed on a Zetasizer 4 (Malvern, Southborough, MA, USA). The average liposomal rhSOD content was about 25 μg/μmol of DPPC. For the final preparation dispersed to the patients liposomes were mixed in sterile 1% Carbopogel 980 (Goodrich, Brussels, Belgium) at a concentration of 1.5 mg lrh-SOD/g of gel.

Interferon

Interferons (IFNs) are proteins made and released by host cells in response to the presence of pathogens such as viruses, bacteria, or parasites, or the presence of tumor cells. Interferons allow for communication between cells to trigger the protective defenses of the immune system that eradicate pathogens or tumors. IFNs belong to the class of glycoproteins known as cytokines. Functions of IFNs include activating immune cells, such as natural killer cells and macrophages; increasing recognition of infection or tumor cells by up-regulating antigen presentation to T lymphocytes; and increasing the ability of uninfected host cells to resist new infection by pathogen. Several distinct IFNs have been identified in mammals, seven of which have been identified in humans. IFNs are typically divided among three IFN classes: Type I IFN, Type II IFN, and Type III IFN. The type I interferons present in humans are IFN-α, IFN-β and IFN-ω.

Several types of INFs are suitable for use in the topical formulations of the invention. Suitable and effective INFs can include, but are not limited to, human leukocyte interferon-alpha (HuIFN-alpha-Le), interferon-alpha, interferon-alpha-2a, interferon-alpha-2b, PEGylated interferon-alpha, PEGylated interferon-alpha-2a, PEGylated interferon-alpha-2b, interferon-beta 1a, liquid form, interferon-beta 1a, lyophilized, interferon-beta 1a biogeneric, interferon-beta 1b, interferon-beta 1b biosimilar, and the like. About 0.01 wt. % to about 5 wt. % of an INF active can be included in a formulation. In some embodiments, a dose of $1-10\times10^6$ U interferon (1-6r$10^6$ IU) can be included in a formulation. In other embodiments, a dose of about $2\times10^6$ U interferon, about $4\times10^6$ U interferon, or about $6\times10^6$ U interferon can be included in a formulation. About 1-10 million units, or about 5 million units, of the interferon can typically be included in one dosage unit of the formulation. The INF can be combined with a carrier prior to combining with emu oil and other components of a formulation.

Optional Active Ingredients

The formulations described herein can also include one or more additional actives in varying amounts, according to the desired purpose. In other embodiments, one active, such as nicardipine, can be replaced by one or more other actives. Such additional or replacement actives can include, but are not limited to, carnitine, acyl esters of carnitine such as acetyl-L-carnitine or propionyl-L-carnitine, *Aloe vera* extracts, colchicine, dexamethasone, hydrocortisone, interferons (INF) such as interferon alpha2 or modified versions thereof such as pegylated interferon alpha-2a or pegylated interferon alpha-2b, magnesium sulfate, para-aminobenzoic acid (PABA), potassium para-aminobenzoate (e.g., Potaba®), pentoxifylline, phosphodiesterase type 5 inhibitors, sildenafil citrate, vitamin E, or a combination thereof. Typically, about 0.1 wt. % to about 20 wt. % of each additional active can be included in a formulation.

The concentration of any active agent in the formulation will typically depend upon a variety of factors, including the specific disease or condition to be treated, the nature and activity of the active agent, the desired effect, possible adverse reactions, the ability and speed of the active agent to reach its intended target, and other factors within the particular knowledge of the patient and physician. Preferred formulations will typically contain on the order of about 0.1-50 wt. %, or about 5-30 wt. %, of each active agent.

Penetration Enhancers

The compositions described herein can optionally include one or more penetration enhancers. The penetration enhancer can be, for example, a pharmaceutically acceptable inorganic or an organic base. Examples of inorganic bases include inorganic hydroxides, inorganic oxides, inorganic salts of weak acids, and combinations thereof. Suitable organic bases can include one or more nitrogenous bases.

The body surface can be exposed to a composition described herein that includes a penetration enhancer, such as a base or basic solution or other agent described below, for a sufficient period of time so as to provide a high pH at the skin surface (e.g., a pH of about 7.5 to about 12), thus creating channels in the skin or mucosa for the drug to pass through. The drug flux can be proportional to the strength of the solution and the duration of exposure. The composition can also include at least one irritation-mitigating additive.

The compositions and methods described herein can provide an enhanced flux of an active agent in the range of at least about 2-fold to about 10-fold, preferably at least about 10-fold to 50-fold, or at least about 50-fold to 100-fold, as compared to the flux observed in the absence of the emu oil or a penetration enhancer described herein.

While emu oil provides enhanced permeation of the active compared to standard topical formulations, a secondary penetration enhancer can be included in any composition described herein, according to various embodiments.

Examples of classes of suitable secondary enhancers (or "co-enhancers") include, but are not limited to, fatty acids, saturated and/or unsaturated; fatty alcohols; bile acids; non-ionic surfactants, including esters of fatty acids, fatty (long-chain alkyl or alkenyl) esters of monohydric alcohols, diols, and polyols, diols and polyols that are both esterified with a fatty acid and/or substituted with a polyoxyalkylene, polyoxyalkylene fatty acid esters, polyoxyalkylene fatty ethers, polyoxyalkylene fatty ethers, and polyglyceryl fatty acid esters; amines; amides; N-alkyl-azacycloalkanones, or N-alkyl-azacycloalkenones; hydrocarbon solvents; terpenes; lower alkyl esters; cyclodextrin enhancers; nitrogen-containing heterocycles; sulfoxides; urea and its derivatives, or combinations thereof.

Specific examples of suitable co-enhancers include ethers such as diethylene glycol monoethyl ether (available commercially as Transcutol®, Gattefosse SA) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin; alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as polyethylene glycol, and polyethylene glycol monolaurate; amides and other nitrogenous compounds such as urea, dimethylacetamide, dimethylformamide, 2-pyrrolidone, 1-methyl-2-pyrrolidone, ethanolamine, diethanolamine and triethanolamine; terpenes; alkanones; and organic acids, particularly citric acid and succinic acid. Azone® and sulfoxides such as dimethylsulfoxide and decylmethylsulfoxide may also be used, but are less preferred. Combinations of one or more of the preceding agents can be added to a composition described herein. *Percutaneous Penetration Enhancers*, eds. Smith et al. (CRC Press, 1995) provides an overview of the field and further information concerning suitable secondary enhancers for use in conjunction with the compositions described herein. Various suitable lipophilic co-enhancers are also described in U.S. Pat. No. 6,835,392 (Hsu et al.) and U.S. Pat. No. 7,205,003 (Maibach et al.). Additional penetration enhancers that can be included are described by Ehdaie (*J. Pharm. Biomed. Sci.*, 1(8), 161-166, 2011).

The composition may also contain irritation-mitigating additives to minimize or eliminate the possibility of skin irritation or damage to sensitive skin resulting from the drug, the base enhancer, or other components of the formulation. Suitable irritation-mitigating additives include, for example: α-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; chloroquine, or combinations thereof. The irritant-mitigating additive, if present, may be incorporated into the formulation at a concentration effective to mitigate irritation or skin damage, typically representing not more than about 20 wt. %, more typically not more than about 5 wt. %, of the formulation, and often about 0.1 to about 3 wt. % of the formulation.

In some embodiments, dimethyl sulfoxide (DMSO) can be included in the composition as a penetration enhancer. DMSO is a rapidly absorbed skin penetrant, with the ability to carry other substances through membranes such as skin, while it acts as an anti-inflammatory agent. Active agents dissolved in DMSO retain their therapeutic activity and their specific properties over a prolonged period of time; it can maintain and multiply the activity of the active it carries. Allergic reactions can be diminished by the inclusion of DMSO. Any detectable order of DMSO can be diminished, for example, by using aloe or a mint fragrance.

Treating Peyronie's Disease

As described above, the invention provides a novel medicament useful for the treatment of connective tissue conditions or disorders. Such conditions or disorders include, but are not limited to, sub-dermal plaque formations and accumulations such as Peyronie's disease, Dupuytren's contracture, Ledderhose Fibrosis, and fibrosis of the muscle tissue that underlies erectile dysfunction. This disclosure further provides medicaments useful for the treatment of conditions characterized by the hyperproliferation of connective tissue. Such conditions include, but are not limited to Peyronie's disease, Dupuytren's contracture, Ledderhose Fibrosis, and scarring. Such tissue disorders can be treated by the noninvasive topical application of a formulation described herein.

One important component of a therapeutic formulation disclosed herein can be a calcium channel blocker. A variety of calcium channel blockers are described herein. In combination with one or more other formulation components, such as other active ingredients, emu oil, and suitable carriers for transdermal delivery, the calcium channel blockers can reduce fibrotic tissue disorder symptoms. The invention thus provides compositions and methods for the transdermal administration of calcium channel blockers for the treatment of fibrotic tissue disorders that exhibit subdermal plaque accumulations.

The formulations described herein include topical gels that can effectively treat, and in some cases, reverse, perceptible Peyronie's disease symptoms. Topical application of a formulation described herein can substantial reduce the symptoms to a degree substantially greater and with a substantially higher incidence of success than previously experienced by patient populations treated with many known therapies. For example, the formulations described herein can be highly effective in treating erectile dysfunction cases that are related to fibrosis of cavernosal smooth muscle tissue.

A formulation, such as one of the therapeutic compositions described in the Examples below, e.g., which includes actives such as nicardipine and SOD in an emu oil carrier, can be used to treat not only Peyronie's disease, but also other connective tissue disorders, including Dupuytren's contracture and Ledderhose Fibrosis. The formulations can further be used to treat existing scars, such as those that arise from injury and surgical procedures. The topical emu oil formulations described herein, when applied to existing scars, can substantially reduce the dimension and color aberrations of the scars.

Erectile Dysfunction, Other Fibrotic Disorders, and Scars

Fibrosis is a common response to numerous conditions including tissue necrosis, trauma or injury, connective tissue disease, hypertension, diabetes, arterial insufficiency, and atherosclerosis. Fibrosis of cavernosal smooth muscle tissue can result in loss of elasticity of this smooth muscle tissue, interfering with the normal expansion of the cavernosal chambers when filled with arterial blood, thereby allowing for only a partial penile erection or no erection at all.

Erectile dysfunction due to fibrosis is common after 40 years of age, while the capacity for erection often is not changed. Because fibrosis underlies certain forms of erectile dysfunction, an effective topically applied antioxidant and/or calcium channel blocker formulation can be useful in treating forms of erectile dysfunction that arise from fibrosis because excessive formation of connective tissue is a common causative factor of both fibrosis-related erectile dysfunction and Peyronie's disease.

The use of the formulations described herein in the treatment of fibrosis-related erectile dysfunction can be similar to the use in treating Peyronie's disease. Variations of dosage and periodicity of treatments may be indicated for different conditions and severities.

Conditions such as Dupuytren's contracture of the hand and Ledderhose Fibrosis manifest themselves via sub-dermal plaques. The formulations described herein can be used for treating both Dupuytren's contracture of the hand and Ledderhose Fibrosis. The efficacy in treating Dupuytren's contracture of the hand and Ledderhose Fibrosis through topical application can be similar to that for treating Peyronie's disease.

Another use for the formulations described herein involves the remediation of existing scars. The formulations can exhibit a high degree of efficacy in reducing objective manifestations of scar tissues. The formulations can be applied in a like dosage and periodicity as described herein to a variety of scar types with successful results. Aberrant coloration of existing scars can be substantially reduced. The treatment of existing scarring through use of the topical formulations by application to the scar can provide scar remediation with an unprecedented combination of ease of treatment, lack of pain and efficacy.

Therapeutic Formulations

The invention thus provides compositions suitable for topical application to the skin. The composition can include a calcium channel blocker active agent and/or superoxide dismutase, and emu oil. The composition can further include a pharmaceutically acceptable carrier, in addition to the emu oil, which can itself act as a carrier. The calcium channel blocker can be, for example, nicardipine, verapamil, nifedipine, diltiazem, amalodipine, felodipine, isradipine, nimodipine, nisoldipine, bepridil, or a combination thereof. In one specific embodiment, the calcium channel blocker is nicardipine. In another specific embodiment, the calcium channel blocker is verapamil. The calcium channel blocker can be present, for example, in about 1 wt. % to about 50 wt. %, about 2 wt. % to about 30 wt. %, about 5 wt. % to about 25 wt. %, 10 wt. % to about 25 wt. %, or about 20 wt. %.

The superoxide dismutase can be, for example, orgotein, a superoxide dismutase isolated from *Escherichia coli* or *Saccharomyces cerevisiae*, a liposomally encapsulated recombinant human Cu/Zn-Superoxide Dismutase (lrh-SOD), superoxide dismutase conjugated to polyethylene glycol or to low molecular weight heparin, or a combination thereof. In some embodiments, the superoxide dismutase is a liposomally encapsulated recombinant human Cu/Zn-Superoxide Dismutase (lrhSOD). The superoxide dismutase can be present in about 0.01 wt. % to about 5 wt. %, about 0.1 wt. % to about 2 wt. %, about 0.1 wt. % to about 1 wt. %, about 0.1 wt. % to about 0.5 wt. %, or about 0.2 wt. %.

Emu oil can be present in a formulation in about 10 wt. % to about 99.9 wt. %. In some embodiments, the emu oil is present in about 30 wt. % to about 98 wt. %, 40 wt. % to about 95 wt. %, 50 wt. % to about 90 wt. %, 60 wt. % to about 85 wt. %, or 30 wt. % to about 75 wt. %. For example, in some embodiments the formulation can include about 5 wt. %, about 10 wt. %, about 15 wt. %, or about 20 wt. % of an active agent, such as nicardipine, or verapamil, with the remainder of the formulation being emu oil. Such formulations can also include appropriate amounts (e.g., 0.1-15%, 0.1-5%, or 0.1-5%) of other ingredients such as gelling agents, fragrances, and the like.

In some embodiments, the composition includes a pharmaceutically acceptable carrier of emu oil, mineral oil, ethylene glycol, propylene glycol, polyethylene glycol, propoleum, or a combination thereof. In some embodiments, the pharmaceutically acceptable carrier can be present in about 45 wt. % to about 99 wt. %, or about 45 wt. % to about 70 wt. %. The composition can further comprising a gelling agent, a preservative, a fragrance, or a combination thereof. The composition can be in the form of a gel, cream, foam, lotion, oil, ointment, paste, suspension, or aerosol spray.

In one embodiment, the composition includes about 2 wt. % to about 25 wt. % of a calcium channel blocker, about 40 wt. % to about 98 wt. % emu oil, and 0 wt. % to about 58 wt. % of a pharmaceutically acceptable carrier. In another embodiment, the composition includes about 2 wt. % to about 25 wt. % of nicardipine and/or verapamil, about 40 wt. % to about 97 wt. % emu oil, and about 1 wt. % to about 58 wt. % of mineral oil, polysorbate 80, ethoxy diglycol, or a combination thereof.

In one embodiment, the composition includes about 0.1 wt. % to about 3 wt. % of superoxide dismutase, about 40 wt. % to about 97 wt. % emu oil, and about 1 wt. % to about 60 wt. % of a pharmaceutically acceptable carrier. In another embodiment, the composition includes about 0.2 wt. % to about 2 wt. % of superoxide dismutase, about 40 wt. % to about 97 wt. % emu oil, and about 1 wt. % to about 60 wt. % of mineral oil, polysorbate 80, ethoxy diglycol, or a combination thereof.

In one embodiment, the composition includes about 2 wt. % to about 25 wt. % of a calcium channel blocker, about 0.1 wt. % to about 3 wt. % of superoxide dismutase, about 40 wt. % to about 80 wt. % emu oil, and about 32 wt. % to about 58 wt. % of a pharmaceutically acceptable carrier. In another embodiment, the composition includes about 2 wt. % to about 25 wt. % of nicardipine and/or verapamil, about 0.2 wt. % to about 2 wt. % of superoxide dismutase, about 40 wt. % to about 80 wt. % emu oil, and about 32 wt. % to about 58 wt. % of mineral oil, polysorbate 80, ethoxy diglycol, or a combination thereof.

In one embodiment, the composition includes about 2 wt. % to about 25 wt. % of a calcium channel blocker, about 0.1 wt. % to about 3 wt. % of superoxide dismutase, and about 72 wt. % to about 98 wt. % emu oil. In another embodiment, the composition includes about 2 wt. % to about 25 wt. % of nicardipine and/or verapamil, about 0.2 wt. % to about 2 wt. % of superoxide dismutase, and about 72 wt. % to about 98 wt. % emu oil.

In one embodiment, the composition includes about 2 wt. % to about 25 wt. % of a calcium channel blocker, about 0.1 wt. % to about 3 wt. % of superoxide dismutase, about $1 \times 10^6$ U and about $10 \times 10^6$ U of interferon, and about 71 wt. % to about 98 wt. % emu oil. In another embodiment, the composition includes about 2 wt. % to about 25 wt. % of nicardipine and/or verapamil, about 0.2 wt. % to about 2 wt. % of superoxide dismutase, about $1 \times 10^6$ U and about $10 \times 10^6$ U of interferon, and about 71 wt. % to about 98 wt. % emu oil.

As discussed above, the invention provides methods for treating a connective tissue disorder. The connective tissue disorder can include sub-dermal plaque accumulation or scar tissue. The method can include topically or transdermally administering an effective amount of a composition described herein to a portion of the dermis that overlies the sub-dermal plaque or scar tissue, for a period of time sufficient to reduce the symptoms or severity of the connective tissue disorder. The connective tissue disorder can be Peyronie's disease, Dupuytren's hand contracture, or Ledderhose Fibrosis. The administration can be about once or twice daily for a period of at least three weeks, for about three months, or for about 6 months, or until the symptoms of the condition are sufficiently reduced.

Pharmaceutical Formulations

The therapeutic compositions described herein will typically include emu oil and one or more active agents ("actives"), as described above. The compositions can be combined with other ingredients to provide pharmaceutical formulations. Pharmaceutical formulations will typically include the therapeutic composition, a pharmaceutically acceptable carrier, and optionally one or more additional ingredients that, for example, aid the formation of the desired delivery vehicle of the active. For topical administration, it will generally be desirable to administer the active agent to the skin as a composition or formulation, for example, in combination with a dermatologically acceptable carrier, where the composition or formulation may be a semi-solid, oil, or a liquid. Liquid compositions can be applied from absorbent pads, used to impregnate bandages and other dressings, or sprayed onto the affected area using a pump-type or aerosol sprayer.

A topical composition typically includes an active and a pharmaceutically acceptable carrier for topical administration. The administration can be the topical application of a gel, a jelly, a cream, a lotion, a wax, an ointment, a solution, a paste, an aerosol, a patch, and/or a combination thereof. Suitable pharmaceutically acceptable carriers include, but are not limited to, creams such as Cetaphil Moisturising Cream (Galderma Laboratories, L.P.), QV Cream (Lision Hong), Sorbolene, or the like. In some embodiments, the pharmaceutical acceptable carrier includes a lotion, such as Alpha Keri Moisturizing Lotion (Mentholatum), DermaVeen Moisturizing Lotion (DermaTech Laboratories), QV Skin Lotion (Lision Hong), Cetaphil Moisturizing Lotion (Galderma Laboratories, L.P.), or the like. In any embodiment, the pharmaceutically acceptable carrier can include one or more oils, in place of or in addition to emu oil.

Salts. In cases where actives are sufficiently basic or acidic to form stable nontoxic acid or base salts, administration of the actives as salts may be appropriate. Examples of pharmaceutically acceptable salts are organic acid addition salts formed with acids which form a physiological acceptable anion, for example, tosylate, methanesulfonate, acetate, propionate, citrate, malonate, tartrate, succinate, benzoate, ascorbate, α-ketoglutarate, and α-glycerophosphate. Pharmaceutically acceptable salts can also be mineral acid salts such as hydrochlorides, hydrobromides, and the like. Suitable salts may also be formed as halides, nitrates, phosphates, sulfates, bicarbonates, carbonate salts, and the like.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

Carriers. Active agents can be combined with a pharmaceutically acceptable carrier or diluent to produce a pharmaceutical composition or formulation. In such pharmaceutical formulations, the active agents or therapeutic composition can be combined with a "carrier" that is physiologically compatible with the skin or mucosal tissue of a human or animal to which it is topically administered. Typically the carrier is substantially inactive, with the exception of its intrinsic surfactant properties which may aid in the production of a solution or suspension of the active ingredients. The compositions may include other physiologically active constituents that do not interfere with the efficacy of the active agents in the composition. In some embodiments, the carriers can be liquid or gel-based materials for use in liquid or gel formulations. The specific formulations depend, in part, upon the desired routes or modes of administration.

Suitable carrier materials include any carrier or vehicle commonly used as a base for solutions, dispersions, emulsions, gels, creams, ointment, lotions, pastes, or foams, for topical administration. Examples include emulsifying agents, inert carriers including hydrocarbon bases, emulsifying bases, non-toxic solvents or water-soluble bases.

Many suitable liquid or gel-based carriers are well-known in the art. The carrier should be able to dissolve or disperse an active at an effective level, optionally with the aid of non-toxic surfactants. Examples include water, physiological salt solutions, alcohols (e.g., methanol, ethanol, propanol, or butanol), glycerol, glycols (e.g., ethylene glycol, propylene glycol, or ethoxy diglycol), polyethylene glycol (e.g., MW 400 to 20,000), water-alcohol/glycol blends, and the like. Suitable carriers and diluents for certain embodiments include, for example, water, saline, isotonic saline solutions, for example, phosphate-buffered saline, aqueous dextrose, glycerol, ethoxy diglycol, dimethyl sulfoxide (DMSO), and the like, or combinations thereof.

Suitable carriers further include aqueous and oleaginous carriers such as, for example, white petrolatum, isopropyl myristate, lanolin or lanolin alcohols, mineral oil, fragrant or essential oil, nasturtium extract oil, sorbitan mono-oleate, cetostearyl alcohol (together or in various combinations), and detergents (e.g., polysorbates (Tweens) such as polysorbate 20, 40, 60, or 80; polyoxyl stearate; or sodium lauryl sulfate). One or more carrier materials can be mixed with water to form a lotion, gel, cream, semi-solid composition, or the like. Other suitable carriers include water-in-oil or oil-in-water emulsions and mixtures of emulsifiers and emollients with solvents such as sucrose stearate, sucrose cocoate, sucrose distearate, mineral oil, propylene glycol, 2-ethyl-1,3-hexanediol, polyoxypropylene-15-stearyl ether, water, or combinations thereof. For example, emulsions containing water, glycerol stearate, glycerin, mineral oil, synthetic spermaceti, cetyl alcohol, or combinations thereof, may be used. Preservatives may also be included in the carrier, such as one or more of butylparaben, methylparaben, propylparaben, benzyl alcohol, and ethylene diamine tetraacetate salts. The composition of the carrier can be varied so long as it does not interfere significantly with the pharmacological activity of the active ingredients of the therapeutic composition.

In one embodiment, the carrier can be a PLO gel (pluronic lecithin organogel). PLO gel contains isopropyl palmitate (a non-oleaginous emollient), soy lecithin (mixture of phospholipids), water, and Pluronic F127.

Gelling Agents and Thickening Agents. The compositions described herein can include one or more gelling agents to increase the viscosity of the composition. Examples of gelling agents and thickening agents, include, but are not limited to, fatty acids, fatty acid salts and esters, fatty alcohols, synthetic polymers, modified celluloses, xanthan gum, or combinations thereof. Examples of suitable synthetic polymers include polyethylene glycol (PEG), polyvinylpyrrolidone (PVP), polyvinyl alcohol (PVA), various Pluronics (poloxamers), or carbomers (e.g., Carbomer 940 or Carbomer 934). Examples of suitable modified celluloses include methylcellulose, carboxymethylcellulose (CMC), hydroxyethylcellulose (HEC), hydroxymethyl cellulose (HMC), hydroxypropyl cellulose (HPC), hydroxypropylmethylcellulose (HPMC), or other cellulose-based gelling agents.

A variety of gelling agents is commercially available and can be obtained in many suitable molecular weights and ranges. For example, the molecular weights of the gelling agent can be about 1 kDa to about 1,000 kDa, about 10 kDa to about 1,000 kDa, about 100 kDa to about 1,000 kDa, or about 50 kDa to about 500 kDa.

Examples of thickening agents include lanolin, hard paraffin, liquid paraffin, white petrolatum, soft yellow paraffin or soft white paraffin, white beeswax, yellow beeswax, propolis (propoleum), cetostearyl alcohol, cetyl alcohol, dimethicones, emulsifying waxes, microcrystalline wax, oleyl alcohol and stearyl alcohol.

A gelling agent or thickening agent can be present in a formulation at about 0.05 wt. % to about 20 wt. %, typically about 0.1 wt. % to about 10 wt. %, about 0.1 wt. % to about 5 wt. %, about 0.5 wt. % to about 2 wt. %, about 0.8 wt. % to about 2 wt. %, or about 1-1.5 wt. %. One or more gelling agents or thickening agents may be included in a single formulation. Such agents can be employed with liquid carriers to form spreadable gels, pastes, ointments, soaps, and the like, for application directly to the skin of the user.

Solutions and Dispersions. Solutions of an active or its salts can be prepared in water, optionally mixed with a nontoxic surfactant. Dispersions can be prepared in glycerol, liquid polyethylene glycols, triacetin, or in a pharmaceutically acceptable oil such as emu oil, or mixtures thereof. Under ordinary conditions of storage and use, preparations may contain a preservative to prevent the growth of microorganisms.

Pharmaceutical dosage forms can include sterile aqueous solutions or dispersions comprising the active ingredient adapted for the extemporaneous preparation of sterile solutions or dispersions, optionally encapsulated in liposomes. The ultimate dosage form should be fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, emu oil, nontoxic glyceryl esters, and suitable mixtures thereof. The proper fluidity of the composition can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the compositions can be brought about by agents delaying absorption, for example, aluminum monostearate and/or gelatin.

Solutions can be prepared by incorporating the active in a desired amount in the appropriate solvent or oil with various other ingredients enumerated herein, as desired, followed by optional filter sterilization. For powders used in the preparation of solutions, methods of preparation can include vacuum drying and freeze drying techniques, which yield a powder of the active plus any additional desired ingredient present in the prepared solutions.

Gels. Gels are clear, sticky, jelly-like semisolids or solids prepared from high molecular weight polymers in an aqueous or alcoholic base. Alcoholic gels are often drying and cooling. Non-alcoholic gels are more lubricating. Gels or jellies can be produced using a suitable gelling agent including, but not limited to, gelatin, tragacanth, a carbomer, or a cellulose derivative and may include glycerol as a humectant, an emollient, and/or a preservative. In some embodiments, gel formulations will include the same or similar ingredients as a solution or dispersion, with the addition of a gelling agent.

The gel can include a nonionic copolymer gelling agent. In one embodiment, the gelling agent is a nonionic polyoxyethylene-polyoxypropylene copolymer gel, for example, a Pluronic gel such as Pluronic F-127 (BASF Corp.), to provide a pluronic gel-based formulation. This gel can be advantageous because it is a liquid at low temperatures but rapidly sets at physiological temperatures, which confines the release of the agent to the site of application or immediately adjacent that site. Other formulations can be carboxymethylcellulose (CMC)-based formulations, hydroxymethyl cellulose (HMC)-based formulations, hydroxypropyl cellulose (HPC)-based formulations, or hydroxypropylmethylcellulose (HPMC)-based formulations, and the like.

Creams. Creams are viscous liquids or semisolid emulsions, either oil-in-water or water-in-oil. Cream bases are water-washable, and comprise an oil phase, an emulsifier, and an aqueous-phase. Water-in-oil creams may be formulated by using a suitable emulsifying agent with properties similar, but not limited, to those of the fatty alcohols such as cetyl alcohol or cetostearyl alcohol and to emulsifying wax. Oil-in-water creams may be formulated using an emulsifying agent such as cetomacrogol emulsifying wax. Suitable properties include the ability to modify the viscosity of the emulsion and both physical and chemical stability over a wide range of pH. The water soluble or miscible cream base may contain a preservative system and may also be buffered to maintain an acceptable physiological pH.

The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant (a substance, such as glycerin, sorbitol, or urea, that absorbs or helps another substance retain moisture).

The emulsifier in a cream formulation is generally a nonionic, anionic, cationic, or amphoteric surfactant. Examples of emulsifiers include, but are not limited to, fatty alcohol polyoxyethylene ether (Peregal A-20), stearates such as polyoxylstearate (Softener SG), glyceryl stearate and pegylated forms of glyceryl stearate such as PEG-5 glyceryl stearate, cetyl alcohol, dithranol, or a combination thereof.

Oil-phase ingredients can include, but are not limited to, dimethicone, dimethiconol, cyclomethicone, diisopropyl adipate, cetyl alcohol, stearyl alcohol, paraffin, petrolatum, almond oil, stearic acid, or a combination thereof. In particular aspects, aqueous ingredients can include, but are not limited to, purified water, glycerol (glycerin), propylene glycol, ethyl paraben, a humectant, or a combination thereof.

In some embodiments, the cream further comprises one or more film formers including but not limiting to polyglycerylmethacrylate, acrylates/$C_{10}$-$C_{30}$ alkyl acrylate cross-polymers; antioxidant including but not limiting to tocopheryl acetate; preservatives including but not limiting to phenoxyethanol, benzyl alcohol; other additives including but not limiting to dicaprylyl ether, disodium EDTA, sodium hydroxide, and lactic acid.

In one embodiment, the cream can include purified water, polyglycerylmethacrylate, propylene glycol, petrolatum, dicaprylyl ether, PEG-5 glyceryl stearate, glycerin, dimethicone, dimethiconol, cetyl alcohol, sweet almond oil, acrylates/$C_{10}$-$C_{30}$ alkyl acrylate cross-polymers, tocopheryl acetate, phenoxyethanol, benzyl alcohol, disodium EDTA, sodium hydroxide, lactic acid, or any combination thereof.

In another embodiment, the cream can include glycerol, light liquid paraffin, soft white paraffin, dimethicone, squalane, methyl hydroxybenzoate, dichlorobenzyl alcohol, or any combination thereof.

Ointments. Ointments are semisolid preparations that include the active incorporated into a fatty, waxy, or synthetic base. Ointments are typically based on petrolatum or other petroleum derivatives. The specific ointment base to be used, as will be appreciated by those skilled in the art, is one that will provide for suitable drug delivery and other desired characteristics such as emolliency or the like. As with other carriers or vehicles, an ointment base is typically inert, stable, non-irritating and non-sensitizing.

Ointment bases may be generally grouped in four classes: oleaginous bases; emulsifiable bases; emulsion bases; and water-soluble bases. Oleaginous ointment bases can include, for example, vegetable oils, fats obtained from animals such as emu oil, and semisolid hydrocarbons obtained from petroleum. Emulsifiable ointment bases, also known as absorbent ointment bases, contain little or no water and can include, for example, hydroxystearin sulfate, anhydrous lanolin, and hydrophilic petrolatum. Emulsion ointment bases are either water-in-oil (W/O) emulsions or oil-in-water (O/W) emulsions, and the oil components can include, for example, cetyl alcohol, glyceryl monostearate, lanolin, and stearic acid. Water-soluble ointment bases can be prepared from polyethylene glycols of varying molecular weight.

Lotions. Lotions are liquid or semiliquid preparations in which solid particles, including the active agent(s), are present in a water or alcohol base. Lotions are usually suspensions of solids, and can include a liquid oily emulsion of the oil-in-water type. Lotions are often desirable formulations because of the ease of applying a more fluid composition. It is generally advantageous for the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Pastes. Pastes are semisolid dosage forms in which the active agent is suspended in a suitable base. Depending on the nature of the base, pastes are divided between fatty pastes or those made from a single-phase aqueous gel. The base in a fatty paste is generally petrolatum, hydrophilic petrolatum, or the like. The pastes made from single-phase aqueous gels generally incorporate carboxymethylcellulose or the like as a base.

Foams. Foam preparations may be formulated to be delivered from a pressurized aerosol canister, via a suitable applicator, using inert propellants. Suitable excipients for the formulation of the foam base include, but are not limited to, propylene glycol, emulsifying wax, cetyl alcohol, and glyceryl stearate. Potential preservatives include methylparaben and propylparaben.

Accordingly, the composition described herein may be formulated for any desired form of topical or transdermal administration, including slow or delayed release preparations. Formulations may include known antioxidants (e.g., vitamin E); buffering agents; lubricants (e.g., synthetic or natural beeswax); sunscreens (e.g., para-aminobenzoic acid); and cosmetic agents (e.g., coloring agents, fragrances, essential oils, moisturizers, or drying agents).

An auxiliary agent such as casein, gelatin, albumin, or sodium alginate may also be included in various formulations. Adjuvants such as fragrances and additional antimicrobial agents can be added to optimize the properties for a given use. Examples of fragrances include Ylang-Ylang oil, lavender oil, powder scent, jasmine, gardenia oil, or green tea oil. In addition, substances such as wetting or emulsifying agents, stabilizing agents, or pH buffering agents, may also be included. When a water-based carrier is used, the composition is typically near a neutral pH (+/− about 1, or 2, pH units).

Further examples of dermatological ingredients and compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the actives described herein in place of other actives.

The compositions described above can be prepared using standard compounding techniques. For example, for a composition that includes nicardipine, verapamil, or a salt of an active, the active can be triturated to reduce particle size. A second active, such as SOD or INF can then be added with a small amount of carrier such as polysorbate 80 and/or ethoxy diglycol to wet the actives. This mixture can then be incorporated into a desired amount of emu oil using principles of geometric dilution until a smooth and uniform suspension is formed. This suspension can then be combined with other ingredients, such as a fragrance, to provide a therapeutic composition. The suspension can also be combined with other ingredients to form a variety of formulations, such as a gel, a jelly, a cream, an ointment, a wax, a lotion, a paste, a foam, or an aerosol. The suspension, or a gel, jelly, cream, ointment, wax, lotion, or paste can also be incorporated into a patch, such as an occlusive patch, to further improve transdermal penetration.

Enhanced Delivery Techniques

Transdermal delivery can be carried out by methods known in the art or as described herein, including, for example, methods directed to 1) the use of chemical penetration enhancers or skin enhancers; 2) liposome-mediated delivery; 3) iontophoresis, also known as transdermal electromotive drug administration; 4) electroporation; 5) sonophoresis (ultrasound waves); 6) mechanical (e.g., microporation) devices, and/or 7) air pressure. Methods suitable for transdermal delivery of the agents described herein can include, for example, methods directed to enhancing the transport of material across the skin pores by increasing the rate of transport across existing pores or by amplifying the number of available skin pores through the creation of artificial pores.

Transdermal delivery can be carried out by the use of chemical or penetration enhancers, including for example, a pharmaceutically acceptable oil of vegetable, nut, synthetic or animal origin including emu oil, ethoxylated oil, PEG, linoleic acid, ethanol, methanol, and/or agents which delipidize the stratum corneum. Suitable oils include meadowfoam oil, castor oil, jojoba oil, corn oil, sunflower oil, sesame oil, and emu oil, all of which may be optionally ethoxylated. Examples include those oils and components described in U.S. Pat. No. 7,291,591 (Fishman); U.S. Pat. No. 7,052,715 (Fishman); U.S. Pat. No. 7,033,998 (Fishman); U.S. Pat. No. 6,951,658 (Pearson et al.); U.S. Pat. No. 6,946,144 (Jordan); U.S. Pat. No. 6,759,056 (Jordan); U.S. Pat. No. 6,750,291 (Kim et al.); U.S. Pat. No. 6,720,001 (Chen et al.); U.S. Pat. No. 6,224,853 (Steel et al.); and U.S. Pat. No. 5,695,779 (Mori). In addition, transdermal patches can be used for the topical or transdermal delivery of a composition described herein. A patch can also be adapted for delivery of dry or lyophilized forms of the compositions described herein, for example, using techniques as described in U.S. Pat. No. 5,983,135 (Avrahami). Other patch technology that can be employed in conjunction with the compositions described herein, e.g., in a reservoir of the patch, include the patch technology described in U.S. Pat. No. 6,835,392 (Hsu et al.).

Transdermal delivery can also be carried out by liposome mediated delivery methods (e.g., delivery facilitated by application of lipophilic membrane compositions). Suitable examples may include those described in U.S. Pat. No. 5,910,306 (Alving et al.); U.S. Pat. No. 5,718,914 (Foldvari); and U.S. Pat. No. 5,064,655 (Uster et al.). Transdermal delivery systems can also be employed in conjunction with a wide variety of iontophoresis or electrotransport systems. Illustrative electrotransport drug delivery systems that can be used in conjunction with the topical formulations herein are described by U.S. Pat. No. 5,147,296 (Theeuwes et al.); U.S. Pat. No. 5,169,382 (Theeuwes et al.); and U.S. Pat. No. 5,169,383 (Gyory et al.).

When a sonophoresis technique is used, one ultrasonic frequency can be applied to the skin, or two or more different ultrasonic frequencies can be applied to the skin (e.g., one low and one high ultrasonic frequency). As with the other techniques described above, this technique can be used in combination with other techniques, such as prior to the topical application of a composition described herein, including the application of a transdermal patch. Iontophoresis or electroporation techniques that can be employed are further described in U.S. Patent Publication No. 2004/0210184 (Kost et al.).

Another transdermal drug delivery technique that can be used in conjunction with the compositions described herein includes employing a device to use air pressure to inject a small stream of the composition through the top layers of the skin without the aid of a needle. The air pressure gun can be the same as or similar to the devise used to provide vaccines to children. Small, disposable pen-like devices are also suitable, as for diabetics who take insulin daily.

Dosing and Administration Procedures

The compositions and formulations described herein typically contain at least 0.1% of an active agent. The percentage of active(s) in the compositions and formulations can vary and may conveniently be about 0.2% to about 50%, about 0.5% to about 40%, about 1% to about 30%, about 2% to about 25%, or about 3% to about 20%, of the weight of a given unit dosage form. The amount of active in such therapeutically useful compositions is such that an effective dosage level can be attained.

Useful dosages of the actives described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of an active, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician. A desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The formulations described herein can be dispensed, for example, from single-dose dispensers or multi-dose dispensers. The dispenser can be, for example, a syringe, a tube, a pump, or any suitable applicator for dispensing the formulation. In some embodiments, the formulation will be provided in multi-dose dispensers, for example, that includes a supply sufficient to last one week, or one month. In other embodiments, the formulation can be provided in 1 mL or 10 mL syringes, optionally graduated at various volume measurements, such as 0.1 mL increments, or 1 mL increments. Each syringe can be, for example, filled to the 1.0 mL mark or 10 mL mark. In one embodiment, one dose (approximately 40 mg) of nicardipine-containing formulation (e.g., a gel) can be contained in 0.5 mL of the composition. Each syringe can be capped with a tip that can be removed and replaced, for example, by simply pushing or pulling with a twist. In some embodiments, the patient can be directed to apply 0.5 mL (40 mg) twice a day, for example, in the morning and in the evening. Thus one syringe can provide enough of a dose for one day. The previous dose should be removed and the area cleaned and dried before a new dose is applied.

The patient can remove the cap and dispel 0.5 mL by pushing the plunger to the 0.5 mL mark as a first dose. The second dose can result from emptying the syringe. The patient can apply the medication by starting at the point where a plaque is concentrated or where a curvature begins. The topical formulation can be spread until the entire penile shaft has been covered with the formulation. The patient's progress should be evaluated every 2-6 weeks to assess the therapy. Application to the entire penile shaft can result in complete reversal of symptoms. During the treatment, each patient's progress should be evaluated on a regular basis, such as at least about every two weeks. If no results occur by the end of the third week, the dose can be increased, the formulation applied more often than twice daily, or a combination thereof.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Therapeutic Topical Formulations

The following are examples of therapeutic compositions that can be used for the effective treatment of, or mitigation of the symptoms of, connective tissue disorders, including Peyronie's disease, Dupuytren's hand contracture, or Ledderhose Fibrosis.

In the various therapeutic compositions described above and in the examples below, the specific active agent can be any one or more of the actives described herein, that can be effective for aiding treatment of connective tissue disorders.

The gelling agent can be replaced with a thickening agent, or a thickening agent can be added in addition to the gelling agent.

A fragrance can be included in any suitable amount (e.g., 0.01% by weight to about 3% by weight) or the fragrance can be omitted from the formulation. The composition can be applied to the skin in any suitable dosing regimen, for example, as recommended by a clinician or medical practitioner. One advantageous dosing schedule can involve applying the compositions twice daily (BID dosing).

| Therapeutic Composition No. 1 | |
|---|---|
| Component | Amount (wt. %) |
| Active Agent | 0.1-30% |
| Carrier | 0-50% |
| Gelling Agent | 0-15% |
| Fragrance | 0-3% |
| Emu Oil | q.s. |

| Therapeutic Composition No. 2 | |
|---|---|
| Component | Amount (wt. %) |
| Nicardipine | 15-25% |
| Carrier | 0-50% |
| Gelling Agent | 0-15% |
| Fragrance | 0-3% |
| Emu Oil | q.s. |

| Therapeutic Composition No. 3 | |
|---|---|
| Component | Amount (wt. %) |
| SOD | 0.1-2% |
| Carrier | 0-50% |
| Gelling Agent | 0-15% |
| Fragrance | 0-3% |
| Emu Oil | q.s. |

| Therapeutic Composition No. 4 | |
|---|---|
| Component | Amount (wt. %) |
| Nicardipine | 15-25% |
| SOD | 0.1-2% |
| Gelling Agent | 0-15% |
| Fragrance | 0-3% |
| Emu Oil | q.s. |

| Therapeutic Composition No. 5 | |
|---|---|
| Component | Amount (wt. %) |
| Nicardipine | 15-25% |
| SOD | 0.1-2% |
| Carrier | 0-50% |
| Gelling Agent | 0-15% |
| Fragrance | 0-3% |
| Emu Oil | q.s. |

| Therapeutic Composition No. 6 | |
| --- | --- |
| Component | Amount (wt. %) |
| Active Agent | 1-25% |
| Carrier | 0.1-50% |
| Gelling Agent | 0.01-15% |
| Fragrance | 0.1-3% |
| Emu Oil | q.s. |

| Therapeutic Composition No. 7 | |
| --- | --- |
| Component | Amount (wt. %) |
| Nicardipine | 15-25% |
| Carrier | 1-50% |
| Gelling Agent | 0.1-15% |
| Fragrance | 0.1-3% |
| Emu Oil | q.s. |

| Therapeutic Composition No. 8 | |
| --- | --- |
| Component | Amount (wt. %) |
| SOD | 0.1-2% |
| Carrier | 1-50% |
| Gelling Agent | 0.1-15% |
| Fragrance | 0.1-3% |
| Emu Oil | q.s. |

| Therapeutic Composition No. 9 | |
| --- | --- |
| Component | Amount (wt. %) |
| Nicardipine | 15-25% |
| SOD | 0.1-2% |
| Gelling Agent | 0.1-15% |
| Fragrance | 0.1-3% |
| Emu Oil | q.s. |

| Therapeutic Composition No. 10 | |
| --- | --- |
| Component | Amount (wt. %) |
| Nicardipine | 15-25% |
| SOD | 0.1-2% |
| Carrier | 1-50% |
| Gelling Agent | 0.1-15% |
| Fragrance | 0.1-3% |
| Emu Oil | q.s. |

| Therapeutic Composition No. 11 | |
| --- | --- |
| Component | Amount (wt. %) |
| Active Agent | 20% |
| Mineral Oil | 0-40% |
| HPC | 0.5-2% |
| Fragrance | 0.1-3% |
| Emu Oil | q.s. |

| Therapeutic Composition No. 12 | |
| --- | --- |
| Component | Amount (wt. %) |
| Nicardipine | 15-25% |
| Mineral Oil | 0-40% |
| HPC | 0.5-2% |
| Fragrance | 0.1-3% |
| Emu Oil | q.s. |

| Therapeutic Composition No. 13 | |
| --- | --- |
| Component | Amount (wt. %) |
| SOD | 0.2% |
| Mineral Oil | 0-40% |
| HPC | 0.5-2% |
| Fragrance | 0.1-3% |
| Emu Oil | q.s. |

| Therapeutic Composition No. 14 | |
| --- | --- |
| Component | Amount (wt. %) |
| Nicardipine | 20% |
| SOD | 0.2% |
| HPC | 0.5-2% |
| Fragrance | 0.1-3% |
| Emu Oil | q.s. |

| Therapeutic Composition No. 15 | |
| --- | --- |
| Component | Amount (wt. %) |
| Nicardipine | 20% |
| HPC | 0.5-2% |
| Fragrance | 0.1-3% |
| Emu Oil | q.s. |

In each of Therapeutic Compositions 1-15, the carrier, when present, can be a suitable topical carrier such as mineral oil, ethylene glycol, propylene glycol, polyethylene glycol, or a combination thereof. The active agent nicardipine can be replaced with a different calcium channel blocker described herein, or partially replaced with a second calcium channel blocker, for example, by up to about 50% of the amount indicated above. Specific examples of alternative Therapeutic Compositions 1-15 are such compositions having nicardipine replaced by verapamil. Other components may be added to the compositions, which can therefore vary the recited weight percents and ranges of components above, for example, by +/−10%, 20%, or 30%. For example, a penetration enhancer can be added in an amount of about 1 wt. % to about 20 wt. %.

Example 2. Therapeutic Topical Formulations

The following are examples of therapeutic compositions that can be used for the effective treatment of, or mitigation of the symptoms of, connective tissue disorders such as Peyronie's disease, Dupuytren's hand contracture, or Ledderhose Fibrosis.

In the various therapeutic compositions described above and in the examples below, the specific active agent can be any one or more of the actives described herein, that can be effective for aiding treatment of connective tissue disorders. The gelling agent can be replaced with a thickening agent, or a thickening agent can be added in addition to the gelling agent.

A fragrance can be included in any suitable amount (e.g., 0.01% by weight to about 3% by weight) or the fragrance can be omitted from the formulation. The composition can be applied to the skin in any suitable dosing regimen, for example, as recommended by a clinician or medical practitioner. One advantageous dosing schedule can involve applying the compositions twice daily (BID dosing).

| Therapeutic Composition No. 16 | |
| --- | --- |
| Component | Amount (wt. %) |
| INF | $1\text{-}10 \times 10^6$ U |
| Carrier | 0-50% |
| Gelling Agent | 0-15% |
| Fragrance | 0-3% |
| Emu Oil | q.s. |

| Therapeutic Composition No. 17 | |
| --- | --- |
| Component | Amount (wt. %) |
| INF | $1\text{-}10 \times 10^6$ U |
| SOD | 0.1-2% |
| Gelling Agent | 0-15% |
| Fragrance | 0-3% |
| Emu Oil | q.s. |

| Therapeutic Composition No. 18 | |
| --- | --- |
| Component | Amount (wt. %) |
| INF | $1\text{-}10 \times 10^6$ U |
| SOD | 0.1-2% |
| Carrier | 0-50% |
| Gelling Agent | 0-15% |
| Fragrance | 0-3% |
| Emu Oil | q.s. |

| Therapeutic Composition No. 19 | |
| --- | --- |
| Component | Amount (wt. %) |
| INF α | $1\text{-}6 \times 10^6$ U |
| Carrier | 1-50% |
| Gelling Agent | 0.1-15% |
| Fragrance | 0.1-3% |
| Emu Oil | q.s. |

| Therapeutic Composition No. 20 | |
| --- | --- |
| Component | Amount (wt. %) |
| INF α | $1\text{-}6 \times 10^6$ U |
| SOD | 0.1-2% |
| Gelling Agent | 0.1-15% |
| Fragrance | 0.1-3% |
| Emu Oil | q.s. |

| Therapeutic Composition No. 21 | |
| --- | --- |
| Component | Amount (wt. %) |
| INF α | $1\text{-}6 \times 10^6$ U |
| SOD | 0.1-2% |
| Carrier | 1-50% |
| Gelling Agent | 0.1-15% |
| Fragrance | 0.1-3% |
| Emu Oil | q.s. |

| Therapeutic Composition No. 22 | |
| --- | --- |
| Component | Amount (wt. %) |
| INF α-2a | $1\text{-}6 \times 10^6$ U |
| Mineral Oil | 0-40% |
| HPC | 0.5-2% |
| Fragrance | 0.1-3% |
| Emu Oil | q.s. |

| Therapeutic Composition No. 23 | |
| --- | --- |
| Component | Amount (wt. %) |
| INF α-2a | $2 \times 10^6$ U |
| SOD | 0.2% |
| HPC | 0.5-2% |
| Fragrance | 0.1-3% |
| Emu Oil | q.s. |

| Therapeutic Composition No. 24 | |
| --- | --- |
| Component | Amount (wt. %) |
| INF α-2a | $2 \times 10^6$ U |
| SOD | 0.2% |
| Mineral Oil | 0-40% |
| HPC | 0.5-2% |
| Fragrance | 0.1-3% |
| Emu Oil | q.s. |

In each of Therapeutic Compositions 16-24, the carrier, when present, can be a suitable topical carrier such as mineral oil, ethylene glycol, propylene glycol, polyethylene glycol, or a combination thereof. The active agent can be replace with a different interferon described herein, or partially replaced with a interferon, for example, by up to about 50% of the amount indicated above. Other components may be added to the compositions, which can therefore vary the recited weight percents and ranges of components above, for example, by +/−10%, 20%, or 30%. For example, a penetration enhancer can be added in an amount of about 1 wt. % to about 20 wt. %.

Example 3. Therapeutic Topical Formulations

The following are examples of therapeutic compositions that can be used for the effective treatment of, or mitigation of the symptoms of, connective tissue disorders such as Peyronie's disease, Dupuytren's hand contracture, or Ledderhose Fibrosis.

In the various therapeutic compositions described above and in the examples below, a specific active agent can be replaced by any one or more of the actives described herein, that can be effective for aiding treatment of connective tissue disorders. The gelling agent can be replaced with a thickening agent, or a thickening agent can be added in addition to the gelling agent.

A fragrance can be included in any suitable amount (e.g., 0.01% by weight to about 3% by weight) or the fragrance can be omitted from the formulation, i.e., the specific active can be replaced with another active described herein. The composition can be applied to the skin in any suitable dosing regimen recommended by a practitioner. For example, the compositions can be applied twice daily (BID dosing).

| Therapeutic Composition No. 25 | |
|---|---|
| Component | Amount (wt. %) |
| Nicardipine | 15-25% |
| SOD | 0.1-2% |
| INF | 1-10 × $10^6$ U |
| Carrier | 0-50% |
| Gelling Agent | 0-15% |
| Fragrance | 0-3% |
| Emu Oil | q.s. |

| Therapeutic Composition No. 26 | |
|---|---|
| Component | Amount (wt. %) |
| Nicardipine | 15-25% |
| SOD | 0.1-2% |
| INF | 1-10 × $10^6$ U |
| Carrier | 0.1-50% |
| Gelling Agent | 0.1-15% |
| Fragrance | 0.1-3% |
| Emu Oil | q.s. |

| Therapeutic Composition No. 27 | |
|---|---|
| Component | Amount (wt. %) |
| Nicardipine | 15-25% |
| SOD | 0.1-2% |
| INF α | 1-10 × $10^6$ U |
| Active Agent | 0.1-25% |
| Carrier | 0.1-50% |
| Gelling Agent | 0.1-15% |
| Fragrance | 0.1-3% |
| Emu Oil | q.s. |

| Therapeutic Composition No. 28 | |
|---|---|
| Component | Amount (wt. %) |
| Nicardipine | 15-25% |
| SOD | 0.1-2% |
| INF α | 1-10 × $10^6$ U |
| Active Agent | 1-25% |
| Carrier | 1-50% |
| Gelling Agent | 0.1-3% |
| Fragrance | 0.1-3% |
| Emu Oil | q.s. |

| Therapeutic Composition No. 29 | |
|---|---|
| Component | Amount (wt. %) |
| Nicardipine | 20% |
| SOD | 0.1-2% |
| INF α | 1-6 × $10^6$ U |
| Mineral Oil | 1-50% |
| HPC | 0.1-3% |
| Fragrance | 0.1-3% |
| Emu Oil | q.s. |

| Therapeutic Composition No. 30 | |
|---|---|
| Component | Amount (wt. %) |
| Nicardipine | 20% |
| SOD | 0.2% |
| INF α | 4 × $10^6$ U |
| Mineral Oil | 0-40% |
| HPC | 0.5-2% |
| Fragrance | 0.1-3% |
| Emu Oil | q.s. |

In each of Therapeutic Compositions 25-30, the carrier, when present, can be a suitable topical carrier such as mineral oil, ethylene glycol, propylene glycol, polyethylene glycol, or a combination thereof. Specific examples of alternative Therapeutic Compositions 25-30 are such compositions having nicardipine replaced by verapamil. Other components may be added to the compositions, which can therefore vary the recited weight percents and ranges of components above, for example, by +/−10%, 20%, or 30%. For example, a penetration enhancer can be added in an amount of about 1 wt. % to about 20 wt. %.

Example 4. Specific Therapeutic Topical Nicardipine Formulations

Three specific topical nicardipine formulations are described below.

| Formulation H-100. | | | | |
|---|---|---|---|---|
| | Nicardipine | SOD | Gel[1] | Fragrance[2] |
| Total dose (mL)[3] | 0.5 | 0.5 | 0.5 | 0.1 |
| % of component | 20% | 0.2% | ~1% | ~0 |
| Single dose (grams) | 0.1 | 0.001 | 0.005 | 0 |
| Emu Oil - | | | | |
| Total dose (mL) | 0.5 | NB: Emu Oil is QS to 100% of total dose | | |
| % of component | 78.8% | | | |
| Single dose (mL) | 0.394 | | | |

| Formulation H-100A. | | | | |
|---|---|---|---|---|
| | Nicardipine | SOD | Gel[1] | Fragrance[2] |
| Total dose (mL)[3] | 0.5 | 0.5 | 0.5 | 0.1 |
| % of component | 18% | 0.2% | ~1% | ~0 |
| Single dose (grams) | 0.09 | 0.001 | 0.005 | 0 |

-continued

Emu Oil -

| | | |
|---|---|---|
| Total dose (mL) | 0.5 | NB: Emu Oil is QS to 100% |
| % of component | 80.8% | of total dose |
| Single dose (mL) | 0.404 | |

Formulation H-100B.

| | Nicardipine | SOD | Gel[1] | Fragrance[2] |
|---|---|---|---|---|
| Total dose (mL)[3] | 0.5 | 0.5 | 0.5 | 0.1 |
| % of component | 15% | 0.2% | ~1% | ~0 |
| Single dose (grams) | 0.075 | 0.001 | 0.005 | 0 |

Emu Oil -

| | | |
|---|---|---|
| Total dose (mL) | 0.5 | NB: Emu Oil is QS to 100% |
| % of component | 83.8% | of total dose |
| Single dose (mL) | 0.419 | |

[1]The amount of gelling agent can vary, depending on the desired viscosity, e.g., 0.1%-1.5%.
[2]Only a trace amount of fragrance is needed, up to approximately 0.5%; add to desired detection level; e.g., 0.0001% to about 0.5%.
[3]Total dose can be for one of two treatments per day.

Example 5. Therapeutic Topical Nicardipine Formulations

A nicardipine-based gel can include, for example, carriers such as emu oil, lecithin isopropyl myristate, and/or Pluronic F127 to form a gel. Methods for preparing various topical gel formulations can be carried out as described below.

In one embodiment, a therapeutic formulation can include nicardipine and SOD as active agents, and a combination of one or more carriers such as emu oil, ethoxy diglycol, poloxamer 407 (Pluronic F127), lecithin, isopropyl myristate, potassium sorbate, sorbic acid powder, and water. The one or more carriers can be used as a vehicle for the actives. One vehicle can include the lecithin carrier vehicle of Table 4-1.

TABLE 4-1

Lecithin Carrier Vehicle.
Ingredients for 1.1 L of a lecithin carrier:

| | | |
|---|---|---|
| 1. | Lecithin, NF | 500 g |
| 2. | Isopropyl Myristate, NF (Cosmetic Grade) | 530 mL |
| 3. | Sorbic Acid, NF-FCC Powder | 2.5-3 g |

The lecithin and sorbic acid are placed in a container sufficient to hold 2 L of liquid. Isopropyl myristate and optionally emu oil (e.g., 100-900 mL) are poured over the lecithin and sorbic acid to disperse the solids. The mixture is then covered and allowed to sit at room temperature until a smooth viscous liquid is formed. The viscous liquid is then stirred and transferred to an amber, light-resistant glass container.

Another carrier vehicle can include a poloxamer carrier of Table 4-2. The poloxamer carrier can be used in combination with the lecithin carrier, or the carriers can be used separately as vehicles for the active agents.

TABLE 4-2

Poloxamer Carrier Vehicle.
Ingredients for 0.8 L of a poloxamer 407 carrier:

| | | |
|---|---|---|
| 1. | Poloxamer 407 (Pluronic F127) | 160 g |
| 2. | Potassium Sorbate, NF | 2-2.5 g |
| 3. | Sterile Water for Irrigation | q.s. 800 mL |

The poloxamer 407 (Pluronic F127) and the potassium sorbate are placed in a 1 L container. The water is poured over these reagents until the volume of the container is about 800 mL. The contents are stirred until the dry reagents are dissolved or evenly dispersed, and the contents are refrigerated. The mixture is allowed to stand until all reagents have dissolved in the water. Additional water sufficient to yield 800 mL can be added. The mixture is stirred and transfer to a clean container. This reagent is preferably stored in a refrigerator.

Preparation of Topical Nicardipine Formulation 4-1 (80 mg/mL Nicardipine Active).

1. Place 4.8 g of nicardipine in a 100 mL beaker. Add 7 mL ethoxy diglycol to the nicardipine and stir well.
2. Place the nicardipine/ethoxy diglycol mixture on a hot plate that has been pre-heated to about 60-80° C. Stir until the nicardipine is dissolved.
3. Remove the nicardipine solution from the hot plate and add about 15 mL of the lecithin-isopropyl myristate carrier and stir well. Optionally add in additional actives and/or emu oil. Transfer the nicardipine/lecithin isopropyl myristate suspension from the beaker to a syringe.
4. Draw up about 35 mL of the poloxamer 407 (Pluronic F127) carrier into a second syringe. Using a Luer Lock To Luer Lock Adapter (e.g., Baxa 13901), attach two 60 cc syringes containing the reagent mixtures (one syringe to each side of the adapter) to mix the two components together.
5. Force the materials from one syringe to the other, repeating the process several times, until a smooth mixture is prepared. The final mixture can have a pH of about 5.8-6.2. A phosphate buffer solution can be used to adjust the pH of the formulation to the desired point.
6. Remove the Luer Lock To Luer Lock Adapter from the syringe containing the nicardipine mixture and cap the syringe. Protect the formulation from light.
7. Dispense in 0.5 or 1.0 mL darkened or opaque containers fitted with an adequate cap for patient use. Label and/or provide patient information sheets having appropriate instructions.

Patients can be instructed to protect the formulation from light and informed that the product is for external use only. The patient can be instructed to avoid vitamin C supplements and anthocyanins while using the medication. Furthermore, patients can be instructed to take at least about 500 mg of a calcium supplement twice a day with food with water, and to take about 50 mg of a zinc supplement once a day with food.

Other topical medicaments useful for treating connective tissue disorders can be based on the preparation of the nicardipine gel described above. A compounding pharmacist of skill in the art can readily prepare variations of the formulations described herein.

Example 6. Pharmaceutical Dosage Forms

The following formulations illustrate representative pharmaceutical dosage forms that may be used for the therapeutic or prophylactic administration of a formulation described herein, such as Therapeutic Compositions 1-30 described above (referred to below as 'Composition X'):

| (i) | |
|---|---|
| Topical Gel 1 | wt. % |
| 'Composition X' | 50% |
| Carbomer 934 | 1.25% |
| Triethanolamine (pH adjustment to 5-7) | q.s. |
| Methyl paraben | 0.2% |
| Emu Oil | q.s. to 100 g |

| (ii) | |
|---|---|
| Topical Gel 2 | wt. % |
| 'Composition X' | 50% |
| Methylcellulose | 2% |
| Methyl paraben | 0.2% |
| Propyl paraben | 0.02% |
| Emu Oil | q.s. to 100 g |

| (iii) | |
|---|---|
| Topical Ointment | wt. % |
| 'Composition X' | 50% |
| Propylene glycol | 1% |
| Anhydrous ointment base | 40% |
| Polysorbate 80 | 2% |
| Methyl paraben | 0.2% |
| Emu Oil | q.s. to 100 g |

| (iv) | |
|---|---|
| Topical Cream 1 | wt. % |
| 'Composition X' | 50% |
| White bees wax | 10% |
| Liquid paraffin | 30% |
| Benzyl alcohol | 5% |
| Emu Oil | q.s. to 100 g |

| (v) | |
|---|---|
| Topical Cream 2 | wt. % |
| 'Composition X' | 50% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Emu Oil | q.s. to 100 g |

| (vi) | |
|---|---|
| Aerosol | mg/can |
| 'Composition X' | 20 |
| Oleic acid | 10 |
| Trichloromonofluoromethane | 5,000 |
| Dichlorodifluoromethane | 10,000 |
| Dichlorotetrafluoroethane | 5,000 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A composition suitable for topical application to skin comprising 15 wt % to 30 wt. % of a dihydropyridine calcium channel blocker active agent, 0.1 wt. % to 2 wt. % of superoxide dismutase, 60 wt. % to 85 wt. % of emu oil by weight in the total composition and one or more thickening agents, penetration enhancers, or non-superoxide dismutase anti-oxidants.

2. The composition of claim 1 wherein the calcium channel blocker is nicardipine, verapamil, nifedipine, diltiazem, amalodipine, felodipine, isradipine, nimodipine, nisoldipine, bepridil, or a combination thereof.

3. The composition of claim 2 wherein the calcium channel blocker is nicardipine.

4. The composition of claim 1 wherein the thickening agent is present in about 0.05 wt. % to about 20 wt. %.

5. The composition of claim 1 wherein the superoxide dismutase is orgotein, a superoxide dismutase isolated from *Saccharomyces cerevisiae*, a liposomally encapsulated recombinant human Cu/Zn-Superoxide Dismutase (lrh-SOD), superoxide dismutase conjugated to polyethylene glycol or to low molecular weight heparin, or a combination thereof.

6. The composition of claim 5 wherein the superoxide dismutase is a liposomally encapsulated recombinant human Cu/Zn-Superoxide Dismutase (lrhSOD).

7. The composition of claim 1 which comprises the one or more non-superoxide dismutase anti-oxidants.

8. The composition of claim 1 which comprises the one or more penetration enhancers.

9. The composition of claim 1 wherein the emu oil is present in about 75 wt. %.

10. The composition of claim 1 further comprising a pharmaceutically acceptable carrier.

11. The composition of claim 10 wherein the pharmaceutically acceptable carrier is present in at least about 5 wt. %.

12. The composition of claim 1 further comprising a preservative, a fragrance, or a combination thereof.

13. The composition of claim 1 wherein the composition is a gel, cream, foam, lotion, oil, ointment, paste, suspension, or aerosol spray.

14. The composition of claim 1 comprising up to about 25 wt. % of the calcium channel blocker.

15. The composition of claim 1 further comprising at least about 0.5 wt. % of mineral oil, polysorbate 80, ethoxy diglycol, ethylene glycol, propylene glycol, polyethylene glycol, propoleum, or a combination thereof.

16. The composition of claim 1 comprising 0.2 wt. % to 2 wt. % of superoxide dismutase.

17. A method for treating a connective tissue disorder, wherein the connective tissue disorder comprises sub-dermal plaque accumulation or scar tissue, comprising topically or transdermally administering an effective amount of a composition of claim 1 to a portion of dermis that overlies the sub-dermal plaque or scar tissue, for a period of time sufficient to reduce symptoms or severity of the connective tissue disorder.

18. The method of claim 17 wherein the connective tissue disorder comprises Peyronie's disease, Dupuytren's hand contracture, or Ledderhose Fibrosis.

19. The method of claim 18 wherein the administration is about once or twice daily for a period of at least three weeks.

\* \* \* \* \*